US008609410B2

(12) United States Patent
Nieda et al.

(10) Patent No.: US 8,609,410 B2
(45) Date of Patent: Dec. 17, 2013

(54) METHOD FOR ACTIVATION TREATMENT OF ANTIGEN-PRESENTING CELL

(75) Inventors: Mie Nieda, Tokyo (JP); Manami Isogai, Tokyo (JP); Masashi Takahara, Tokyo (JP); Andrew Nicol, QLD (AU)

(73) Assignee: Medinet Co., Ltd., Yokohama-shi (JP)

( * ) Notice: Subject to any disclaimer, the term of this patent is extended or adjusted under 35 U.S.C. 154(b) by 443 days.

(21) Appl. No.: 12/066,313

(22) PCT Filed: Sep. 5, 2006

(86) PCT No.: PCT/JP2006/317535
§ 371 (c)(1),
(2), (4) Date: Mar. 10, 2008

(87) PCT Pub. No.: WO2007/029689
PCT Pub. Date: Mar. 15, 2007

(65) Prior Publication Data
US 2009/0104161 A1 Apr. 23, 2009

(30) Foreign Application Priority Data

Sep. 8, 2005 (JP) ................................. 2005-295598
Apr. 14, 2006 (JP) ................................. 2006-112571

(51) Int. Cl.
*C12N 5/078* (2010.01)
*C12N 5/0784* (2010.01)

(52) U.S. Cl.
USPC ........................... 435/375; 424/93.7; 435/372

(58) Field of Classification Search
USPC ................................... 435/372, 375; 424/93.7
See application file for complete search history.

(56) References Cited

U.S. PATENT DOCUMENTS

| 6,429,199 B1 * | 8/2002 | Krieg et al. .................. 514/44 R |
| 6,821,778 B1 | 11/2004 | Takamizawa et al. |
| 2003/0133913 A1 * | 7/2003 | Tomai et al. .................. 424/93.7 |
| 2004/0014724 A1 * | 1/2004 | Seaman et al. .................. 514/94 |
| 2007/0190169 A1 | 8/2007 | Nieda et al. |

FOREIGN PATENT DOCUMENTS

WO    WO2006006638    1/2006

OTHER PUBLICATIONS

Lillienfeld-Toal et al. 2005. Coculture with dendritic cells promotes proliferation but not cytotoxic activity of gamma/delta T cells. Immunology Letters 99:103-108.*
von Lillienfeld-Toal et al. Coculture with dendritic cells promotes proliferation but not cytotoxic activity of gamma/delta T cells. Immunology Letters 99 (2005) 103-108.*
Yu Kato, et al., "Targeting of Tumor Cells for Human gammadelta T cells by nonpeptide antigens", Journal of Immunology, vol. 167, No. 9, XP002515585, Nov. 1, 2001, pp. 5092-5098.
Martin Wilhelm, et al., "Gammadelta T cells for immune therapy of patients with lymphoid malignancies", Blood, vol. 102, No. 1, XP002515586, Jul. 1, 2003, pp. 200-206.
Chinese Office Action mailed Aug. 11, 2010 in corresponding Chinese Application No. 200680032855.6.
Sun Lifei et al., "Therapeutic Effects of Tumor Antigen-Pulsed, IL-2 Gene-Modified Dendritic Cells Combined with Low-Dose Cyclophosphamide on Matastatic Lung Carcinoma", Chinese Journal of Cancer Biotherapy, vol. 6, No. 1, Mar. 1999, pp. 45-49 (with English Abstract).
Fumi Miyagawa, et al. "Essential Requirement of Antigen Presentation by Monocyte Lineage Cells for the Activation of Primary Human γδ T Cells by Aminobisphosphonate Antigen[1]." The American Association of Immunologists, vol. 166, (pp. 5508-5514), 2001.
Volker Kunzmann, et al. "Crucial Role of Monocytes in Aminobisphosphonate Recognition by γδ T Cells." Granulocytes, Monocytes and Macrophages, (pp. 38b-39b), Abstract # 3859, 2003.
Volker Kunzmann, et al. "Stimulation of γδ T Cells by Aminobisphosphonates and Induction of Antiplasma Cell Activity in Multiple Myeloma." The American Society of Hematology, Blood, vol. 96 No. 2, (pp. 384-392), Jul. 15, 2000.
Yoshimasa Tanaka, et al. "Bio Clinica" vol. 19 No. 5, (pp. 439-444) 2004, with Partial Translation.
Shigemi Sasawatari, et al. "Jojosaiboyo Kogenteijisaibo (Artificial Antigen Presenting cells; aAPC) no Kaihatsu" The Japanese Society for Immunology Gakujutsu Shukai Kiroku, vol. 35, (pp. I31 with Full Translation, Nov. 15, 2005.
Mie Nieda, et al. "Therapeutic Activation of Vα24+Vβ11+NKT Cells in Human Subjects Results in Highly Coordinated Secondary Activation of Acquired and Innate Immunity" The American Society of Hematology, Blood, vol. 103 No. 2, (pp. 383-389), Jan. 15, 2004.
Lawrence Fong, et al. "Altered Peptide Ligand Vaccination with Flt3 Ligand Expanded Dendritic Cells for Tumor Immunotherapy" www.pnas.org/cgi/doi/10.1073/pnas.141226398, vol. 98 No. 15, (pp. 8809-8814), Jul. 17, 2001.

(Continued)

Primary Examiner — Taeyoon Kim
(74) Attorney, Agent, or Firm — Oblon, Spivak, McClelland, Maier & Neustadt, L.L.P.

(57) ABSTRACT

Activated antigen-presenting cells that can induce immunocytes including disease antigen-specific CD8+ CTLs and/or γδ T cells efficiently in vivo and/or in vitro, a medical composition comprising the activated antigen-presenting cells, a treatment and prevention method using the activated antigen-presenting cells, and an induction method of immunocytes including disease antigen-specific CTLs and/or γδ T cells induced using the activated antigen-presenting cell, immunocytes induced by the above-noted method, a medical composition comprising the immunocytes, and a treatment and prevention method using the immunocytes are provided. By co-pulsing antigen-presenting cells with bisphosphonate in addition to the pulse with a disease antigen, the ratio of disease antigen-specific CD8+ CTLs and/or γδ T cells and the number of the disease antigen-specific CD8+ CTLs and the γδ T cells can be increased, compared with the case where the co-pulse with bisphosphonate is not carried out.

8 Claims, 1 Drawing Sheet

(56) References Cited

OTHER PUBLICATIONS

Shizuo Akira, et al. "Subscribe to nature Reviews Immunology and Save" Immunology, vol. 4 No. 7, 2pp. Jul. 2004.

Masato Okamoto, et al. "Expression of Toll-Like Receptor 4 on dendritic Cells Is Significant for Anticancer Effect of Dendritic Cell-Based Immunotherapy in Combination with an Active Component of OK-432, a Streptococcal Preparation" Cancer Research, vol. 64, (pp. 5461-5470), Aug. 1, 2004.

Jonathan D. Silk, et al. "Utilizing the Adjuvant Properties of CD 1d-Dependent NK T Cells in T Cell-Mediated Immunotherapy" The Journal of Clinical Investigation, vol. 114 No. 12, (pp. 1800-1811), Dec. 2004.

Gloria Gonzalez-Aseguinolaza, et al. "Natural killer T Cell Ligand α-Galactosylceramide Enhances Protective Immunity Induced by Malaria Vaccines" The Journal of Experimental Medicine, vol. 195 No. 5, (pp. 617-624), Mar. 4, 2002.

Hiranmoy Das, et al. "Vγ2Vδ2 T-Cell Receptor-Mediated Recognition of Aminobisphosphonates" The American Society of Hematology, Blood, vol. 98 No. 5, (pp. 1616-1618), Sep. 1, 2001.

Danila Valmori, et al. "An Antigen-Targeted Approach to Adoptive Transfer Therapy of Cancer [1]" Cancer Research, vol. 59, (pp. 2167-2173), May 1, 1999.

Rivoltini L, et al. "Induction of Tumor-Reactive CTL from Peripheral Blood and Tumor-Infiltrating Lymphocytes of Melanoma Patients by in Vitro Stimulation with an Immunodominant Peptide of the Human Melanoma Antigen MART-1" The Journal of Immunology, vol. 154 No. 5, (pp. 2257-2265), Mar. 1, 1995.

Mehta-Damani A, et al. "Generation of Antigen-Specific CD8 + CTLs from Naive Precursors" The Journal of Immunology, vol. 153 No. 3, (pp. 996-1003), Aug. 1, 1994.

Lucia Conti, et al. "Reciprocal Activating Interaction Between Dendritic Cells and Pamidronate-Stimulated γδ T Cells: Role of CD86 and Inflammatory Cytokines[1]" The Journal of Immunology, vol. 174, (pp. 252-260), 2005.

Hans-Juergen Gober, et al. "Human T Cell Receptor γδCells Reconnize Endogenous mevalonate Metabolitets in Tumor Cells" The Journal of Experimental Medicine, vol. 197 No. 2, (pp. 163-168), Jan. 20, 2003.

S Mariani, et al. "Effector γδ T Cells and Tumor Cells as Immune Targets of Zoledronic Acid in Multiple Myeloma" Leukemia, (pp. 1-7), 2005.

Yu Kato, et al. "Requirement of Species-Specific Interactions for the Activation of Human γδT Cells by Pamidronate[1]" The Journal of Immunology, vol. 170, (pp. 3608-3613), 2003.

Kiyoshi Sato, et al. "Cytotoxic Effects of γδ T Cells expanded ex Vivo by a Third Generation Bisphosphonate for Cancer Immunotherapy" International of Journal of Cancer, Tumor Immunology, (pp. 8), Oct. 15, 2001.

Francesca Fiore, et al. "Enhanced ability of Dendritic Cells to Stimulate Innate and Adaptive Immunity on Short-Term Incubation with Zoledronic Acid" The American Society of Hematology, Immunobiology, Blood, vol. 110 No. 3, (pp. 921-927), Aug. 1, 2007.

Manami Isogai, et al., "Study of proliferative capacity and function of γδT cells by dendritic cells pulsed with pamidronate", The 26th Annual Meeting of the Japanese Research Society for Surgical Cancer Immunology, 2005, p. 120 with English translation.

Manami Isogai, et al., "Study of proliferative capacity of γδT cells by dendritic cells pulsed with pamidronate", Japan Society of Clinical Oncology, vol. 39, No. 2, PS165-6, 2004, p. 846 with English translation.

Masashi Takahara, et al., "Study of proliferative capacity and function of γδT cells by dendritic cells pulsed with pamidronate", The 3rd Scientific Meeting of Japanese Research Association for Immunotherapeutics, 2004, p. 6 with English translation.

* cited by examiner

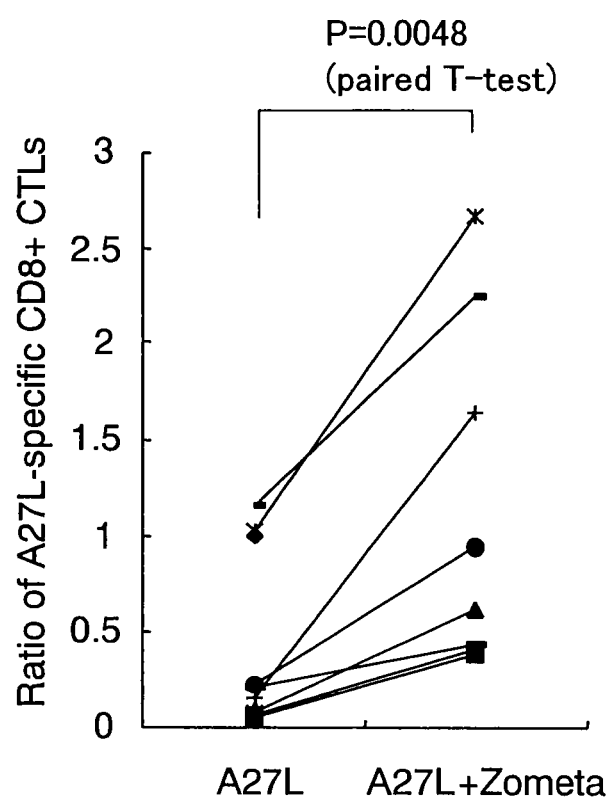

METHOD FOR ACTIVATION TREATMENT OF ANTIGEN-PRESENTING CELL

FIELD OF THE INVENTION

The present invention relates to an antigen-presenting cell that is co-pulsed with bisphosphonate and a disease antigen. Also, the present invention relates to a medical composition comprising the antigen-presenting cell, a treatment and prevention method using the dendritic cell, and an induction method of an immunocyte using the antigen-presenting cell. Further, the present invention relates to an immunocyte that is induced by the induction method, a medical composition comprising the immunocyte, and a treatment and prevention method using the immunocyte.

DESCRIPTION OF THE BACKGROUND

As a method for treating cancer, there have been surgical resection, radiotherapy and chemotherapy using an anti-tumor agent. In recent years, other than these methods, various therapeutic methods have been studied and put into practice. One of them is an immuno-cell therapy utilizing immunocytes.

The immuno-cell therapy includes a LAK (Lymphokine Activated Killer) therapy in which lymphocytes are activated in vitro by lymphokine and then transferred into the body, a CTL (Cytotoxic T Lymphocyte; hereinafter, referred to as CTL) therapy using CTLs that recognize and injure a lesion specifically, a dendritic cell therapy and the like.

In the dendritic cell therapy, using dendritic cells obtained by allowing a disease antigen to be present on MHC (Major Histocompatibility antigen Complex) directly or after intracellular processing, disease antigen-specific CTLs that attack a pathogen selectively are induced in vivo for treatment. The disease antigen to be presented can be, for example, a cancer antigenic protein or peptide, an infectious disease antigenic protein or peptide, or a part thereof (see Non-patent documents 1 and 2, for example).

By co-culturing the dendritic cells pulsed with the disease antigen and lymphocytes so as to stimulate the lymphocytes with the dendritic cells, it is possible to induce disease antigen-specific CTLs in vitro. For example, in the case of using the dendritic cells pulsed with the cancer antigenic protein or peptide or the infectious disease antigenic protein or peptide, an increase in the disease antigen-specific CTLs induced at a co-culture is 5 to 20 times as much as that in the case where the above-noted dendritic cells are not used.

In the dendritic cell therapy using the dendritic cells pulsed with the cancer antigenic protein or peptide or the infectious disease antigenic protein or peptide, the efficiency of induction of the disease antigen-specific CTLs in vivo, namely, the ratio of the CTLs in all the lymphocytes is known to rise by a factor of 2 to 14.

In order to enhance the efficacy of the dendritic cell therapy by raising the efficiency of induction of the disease antigen-specific CTLs by dendritic cells, two methods mainly are conducted at present.

In one method, in addition to pulsing the dendritic cells with the disease antigen, by allowing a drug or the like that reacts with a Toll like receptor (hereinafter, referred to as TLR) on the dendritic cells to react with the dendritic cells so as to enhance an antigen-presenting ability of the dendritic cells, the efficiency of induction of the disease antigen-specific CTLs directly increases (an adjuvant effect via the TLR; see Non-patent documents 3 and 4, for example). In the other method, in addition to pulsing the dendritic cells with the disease antigen, by allowing glycolipid or the like to be present on antigen-presenting molecules other than MHC molecules, for example, CD1d (Cluster Differentiation 1d) molecules on the dendritic cells so as to activate immunocytes including iNKT (invariant Natural Killer T cells), etc. other than the disease antigen-specific CTLs, so that the efficiency of induction of the disease antigen-specific CTLs indirectly increases via these activated immunocytes (an adjuvant effect via the immunocytes other than the disease antigen-specific CTLs; see Non-patent documents 5 and 6, for example).

However, the increase in the disease antigen-specific CTL induction by the direct adjuvant effect via the TLR or the indirect adjuvant effect via the immunocytes other than the disease antigen-specific CTLs is about 4 to 6 times that in the case where these adjuvants are not used (in vitro). Accordingly, it has been desired to develop the technology capable of inducing the disease antigen-specific CTLs more efficiently.

Non-patent document 1: Blood 2004, 103, 383-389
Non-patent document 2: Proc Natl Acad Sci U.S.A. 2001, 98, 8809-8814
Non-patent document 3: Nat Rev Immunol. 2004, 4, 449-511
Non-patent document 4: Cancer Res. 2004, 64, 5461-5470
Non-patent document 5: J Clin Invest. 2004, 114, 1800-1811
Non-patent document 6: J Exp Med. 2002, 195, 617-624

The present invention was made with the foregoing in mind and provides a method for activation treatment of an antigen-presenting cell (for example, a dendritic cell or the like) for efficiently inducing an immunocyte that dominantly includes a disease antigen-specific CD8+ CTL and/or a γδ T cell in vivo and/or in vitro, a medical composition comprising the activated antigen-presenting cell, a treatment and prevention method using the activated antigen-presenting cell, an induction method of an immunocyte that includes a disease antigen-specific CD8+ CTL and/or a γδ T cell using the activated antigen-presenting cell, an immunocyte that is induced by the method, a medical composition comprising the immunocyte, and a treatment and prevention method using the immunocyte.

In order to solve the problem described above, the inventors of the present invention conducted studies. Then, the inventors found that, by co-pulsing dendritic cells with bisphosphonate in addition to the pulse with a disease antigen, the ratios of disease antigen-specific CTLs and γδ T cells to all lymphocytes and the numbers of the disease antigen-specific CTLs and the γδ T cells increased considerably compared with the case of adding no bisphosphonate, and they completed the present invention. For example, by adding bisphosphonate, the ratio of the disease antigen-specific CTLs to all the lymphocytes can increase by a factor of about 100 and the ratio of the γδ T cells to all the lymphocytes can increase by a factor of about 3 compared with those in the case of adding no bisphosphonate, and the number of the disease antigen-specific CTLs can increase by a factor of about 90 and the number of the γδ T cells can increase by a factor of about 6 compared with those in the case of adding no bisphosphonate. However, the present invention is not limited to these numerical values. The present invention promotes further development of the immuno-cell therapy that treats and prevents cancer and/or infectious disease by inducing disease antigen-specific CD8+ CTLs and/or γδ T cells.

SUMMARY OF THE INVENTION

An object of the invention is:
(1) A method for activation treatment of an antigen-presenting cell, the method including co-pulsing the antigen-presenting cell with bisphosphonate and a disease antigen;

(2) the method for activation treatment of an antigen-presenting cell according to (1), wherein the antigen-presenting cell is at least one selected from the group consisting of a dendritic cell, an immature dendritic cell and an artificial antigen-presenting cell;

(3) the method for activation treatment of an antigen-presenting cell according to (1) or (2), wherein the bisphosphonate is a chemical compound represented by the formula (I), a salt thereof or their hydrate,

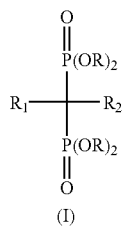

[Formula 1]

where R is a hydrogen atom or a lower alkyl group, $R_1$ and $R_2$ are each, independently of one another, selected from the group consisting of a hydrogen atom, a halogen atom, a hydroxyl group, an amino group, a thiol group, an aryl group or a substituted aryl group, an alkyl group or a substituted alkyl group, a lower alkyl amino group, an aralkyl group, a cycloalkyl group and a heterocyclic group, or $R_1$ and $R_2$ form part of the same cyclic structure, and a substituent in $R_1$ and $R_2$ are selected from the group consisting of a halogen atom, a lower alkyl group, a hydroxyl group, a thiol group, an amino group, an alkoxy group, an aryl group, an arylthio group, an aryloxy group, an alkylthio group, a cycloalkyl group and a heterocyclic group;

(4) the method for activation treatment of an antigen-presenting cell according to any of (1) to (3), wherein the bisphosphonate is at least one selected from the group consisting of a zoledronic acid, a pamidronic acid, an alendronic acid, a risedronic acid, an ibandronic acid, an incadronic acid, an etidronic acid, a salt thereof and their hydrate;

(5) the method for activation treatment of an antigen-presenting cell according to any of (1) to (4), wherein a concentration of the bisphosphonate in the co-pulse is 0.001 to 20 μM;

(6) the method for activation treatment of an antigen-presenting cell according to (5), wherein the concentration of the bisphosphonate in the co-pulse is 0.001 to 5 μM;

(7) the method for activation treatment of an antigen-presenting cell according to any of (1) to (6), wherein the disease antigen is at least one selected from the group consisting of a cancer antigenic protein, a cancer antigenic peptide, an infectious disease antigenic protein or an infectious disease antigenic peptide, a lysed cancer cell or a lysed infectious disease cell, and an apoptotic cell and a necrotic cell of a cancer cell or an infectious disease cell, and a heat-treated product thereof;

(8) the method for activation treatment of an antigen-presenting cell according to any of (1) to (7), wherein a concentration of the disease antigen in the co-pulse is 0.01 to 20 μg/ml;

(9) the method for activation treatment of an antigen-presenting cell according to (8), wherein the concentration of the disease antigen in the co-pulse is 0.1 to 2 μg/ml;

(10) a production method of an activated antigen-presenting cell, the method including treating the antigen-presenting cell with the method for activation treatment according to any of (1) to (9);

(11) an activated antigen-presenting cell produced by the production method according to (10);

(12) a medical composition for a cancer and/or an infectious disease, the medical composition comprising the activated antigen-presenting cell according to (11);

(13) the medical composition according to (12), wherein the antigen-presenting cell is an autologous antigen-presenting cell or an allogeneic antigen-presenting cell that shares the same HLA;

(14) a prevention and treatment method for a cancer and/or an infectious disease, the method including administering the activated antigen-presenting cell according to (11); and

(15) the prevention and treatment method according to (14), wherein the antigen-presenting cell is an autologous antigen-presenting cell or an allogeneic antigen-presenting cell that shares the same HLA.

(16) A method for inducing an immunocyte, the method including (i) co-pulsing an antigen-presenting cell with bisphosphonate and a disease antigen; and (ii) co-culturing the antigen-presenting cell and a lymphocyte simultaneously with or after the co-pulse;

(17) the method for inducing an immunocyte according to (16), wherein the immunocyte to be induced includes at least one of a disease antigen-specific CD8+ CTL and a γδ T cell;

(18) the method for inducing an immunocyte according to (16) or (17), wherein the antigen-presenting cell is at least one selected from the group consisting of a dendritic cell, an immature dendritic cell and an artificial antigen-presenting cell;

(19) the method for inducing an immunocyte according to any of (16) to (18), wherein the bisphosphonate is a chemical compound represented by the formula (I), a salt thereof or their hydrate,

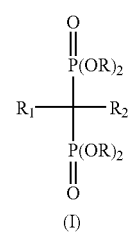

[Formula 1]

where R is a hydrogen atom or a lower alkyl group, $R_1$ and $R_2$ are each, independently of one another, selected from the group consisting of a hydrogen atom, a halogen atom, a hydroxyl group, an amino group, a thiol group, an aryl group or a substituted aryl group, an alkyl group or a substituted alkyl group, a lower alkyl amino group, an aralkyl group, a cycloalkyl group and a heterocyclic group, or $R_1$ and $R_2$ form part of the same cyclic structure, and a substituent in $R_1$ and $R_2$ are selected from the group consisting of a halogen atom, a lower alkyl group, a hydroxyl group, a thiol group, an amino group, an alkoxy group, an aryl group, an arylthio group, an aryloxy group, an alkylthio group, a cycloalkyl group and a heterocyclic group;

(20) the method for inducing an immunocyte according to any of (16) to (19), wherein the bisphosphonate is at least one selected from the group consisting of a zoledronic acid, a pamidronic acid, an alendronic acid, a risedronic acid, an ibandronic acid, an incadronic acid, an etidronic acid, a salt thereof and their hydrate;

(21) the method for inducing an immunocyte according to any of (16) to (20), wherein a concentration of the bisphosphonate in the co-pulse is 0.001 to 20 µM;

(22) the method for inducing an immunocyte according to (21), wherein the concentration of the bisphosphonate in the co-pulse is 0.001 to 5 µM;

(23) the method for inducing an immunocyte according to any of (16) to (22), wherein the disease antigen is at least one selected from the group consisting of a cancer antigenic protein, a cancer antigenic peptide, an infectious disease antigenic protein or an infectious disease antigenic peptide, a lysed cancer cell or a lysed infectious disease cell, and an apoptotic cell and a necrotic cell of a cancer cell or an infectious disease cell, and a heat-treated product thereof;

(24) the method for inducing an immunocyte according to any of (16) to (23), wherein a concentration of the disease antigen in the co-pulse is 0.01 to 20 µg/ml; and

(25) the method for inducing an immunocyte according to (24), wherein the concentration of the disease antigen in the co-pulse is 0.1 to 2 µg/ml.

(26) A production method of an immunocyte, the method including inducing the immunocyte by the method for induction according to any of (16) to (25);

(27) an immunocyte produced by the production method according to (26);

(28) a medical composition for a cancer and/or an infectious disease, the medical composition comprising the immunocyte according to (27);

(29) the medical composition for a cancer and/or an infectious disease according to (28), wherein the antigen-presenting cell is an autologous antigen-presenting cell or an allogeneic antigen-presenting cell that shares the same HLA;

(30) a prevention and treatment method for a cancer and/or an infectious disease, the method including administering the immunocyte according to (27); and

(31) the prevention and treatment method for a cancer and/or an infectious disease according to (30), wherein the antigen-presenting cell is an autologous antigen-presenting cell or an allogeneic antigen-presenting cell that shares the same HLA.

(32) An activation accelerator of an antigen-presenting cell at the time of pulse with a disease antigen, the activation accelerator comprising bisphosphonate as an effective component;

(33) the activation accelerator of an antigen-presenting cell at the time of pulse with a disease antigen according to (32), wherein the antigen-presenting cell is at least one selected from the group consisting of a dendritic cell, an immature dendritic cell and an artificial antigen-presenting cell;

(34) the activation accelerator of an antigen-presenting cell at the time of pulse with a disease antigen according to (32) or (33), wherein the bisphosphonate is a chemical compound represented by the formula (I), a salt thereof or their hydrate,

[Formula 1]

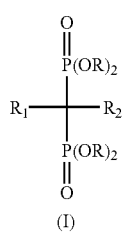

where R is a hydrogen atom or a lower alkyl group, $R_1$ and $R_2$ are each, independently of one another, selected from the group consisting of a hydrogen atom, a halogen atom, a hydroxyl group, an amino group, a thiol group, an aryl group or a substituted aryl group, an alkyl group or a substituted alkyl group, a lower alkyl amino group, an aralkyl group, a cycloalkyl group and a heterocyclic group, or $R_1$ and $R_2$ form part of the same cyclic structure, and a substituent in $R_1$ and $R_2$ are selected from the group consisting of a halogen atom, a lower alkyl group, a hydroxyl group, a thiol group, an amino group, an alkoxy group, an aryl group, an arylthio group, an aryloxy group, an alkylthio group, a cycloalkyl group and a heterocyclic group; and

(35) the activation accelerator of an antigen-presenting cell at the time of pulse with a disease antigen according to any of (32) to (34), wherein the bisphosphonate is at least one selected from the group consisting of a zoledronic acid, a pamidronic acid, an alendronic acid, a risedronic acid, an ibandronic acid, an incadronic acid, an etidronic acid, a salt thereof and their hydrate.

BRIEF DESCRIPTION OF DRAWINGS

FIG. 1 is a graph showing an example of the result of measuring the ratio of A27L-specific CD8+ CTLs.

DESCRIPTION OF THE INVENTION

Unless specifically defined, all technical and scientific terms used herein have the same meaning as commonly understood by a skill artisan in chemistry, biochemistry, cellular biology, molecular biology, and medical sciences.

All methods and materials similar or equivalent to those described herein can be used in the practice or testing of the present invention, with suitable methods and materials being described herein. All publications, patent applications, patents, and other references mentioned herein are incorporated by reference in their entirely. Further, the materials, methods, and examples are illustrative only and are not intended to be limiting, unless otherwise specified.

Embodiment 1

Production of Activated Antigen-Presenting Cells

First, activated antigen-presenting cells of the present invention will be detailed.

The activated antigen-presenting cells of the present invention are antigen-presenting cells that are co-pulsed with bisphosphonate and a disease antigen.

The above-mentioned antigen-presenting cells used in the present invention are not particularly limited but may be any of immature dendritic cells, mature dendritic cells, other antigen-presenting cells, artificial antigen-presenting cells and a mixture thereof, for example. Among them, the immature dendritic cells and the mature dendritic cells are preferable, and the immature dendritic cells are more preferable. This is because, when co-pulsed with bisphosphonate and a disease antigen, the immature dendritic cells more preferably can induce disease antigen-specific CTLs and/or γδ T cells. Also, the above-noted artificial antigen-presenting cells are antigen-presenting cells that are produced artificially and can be, for example, cells that are genetically engineered so as to express at least major histocompatibility antigen (MHC) class I molecules and co-stimulatory molecules (for example, CD80, CD86). Further, the above-noted artificial antigen-presenting cells may be obtained by modifying a tumor-derived cell line so that the MHC class I molecules and the co-stimulatory molecules are expressed as described above. Examples of the above-noted cell line include a breast cancer-derived MDA-MB-231 (class I antigen HLA-A*0201), a renal cancer-derived TUHR10TKB (class I antigen HLA-A*0201/A*2402), a stomach cancer-derived JR-st line (class I antigen HLA-A*2402), and the like. These cell lines are available from ATCC, RIKEN BioResource Center, etc., for example. The production of the artificial antigen-presenting cells mentioned above is disclosed in US Publication US-2005-0048646-A1, and the entire contents thereof are incorporated herein by reference.

In the present invention, bisphosphonate is not particularly limited but refers to a chemical compound that is an analog of a pyrophosphoric acid and obtained by substituting C (a carbon atom) for O (an oxygen atom) in P—O—P of a skeleton of the pyrophosphoric acid. Examples of the bisphosphonate used in the present invention can include a chemical compound represented by the formula (I) below, a salt thereof and their hydrate.

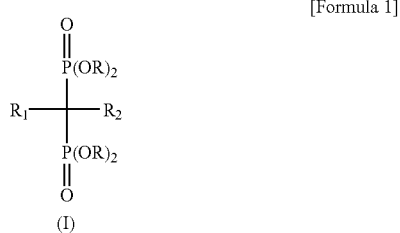

[Formula 1]

In the formula (I) above, R is a hydrogen atom or a lower alkyl group, $R_1$ and $R_2$ are each, independently of one another, selected from the group consisting of a hydrogen atom, a halogen atom, a hydroxyl group, an amino group, a thiol group, an aryl group that may be substituted, an alkyl group that may be substituted, a lower alkyl amino group, an aralkyl group, a cycloalkyl group and a heterocyclic group, and $R_1$ and $R_2$ may form part of the same cyclic structure.

The substituent in $R_1$ and $R_2$ described above are selected from the group consisting of a halogen atom, a lower alkyl group, a hydroxyl group, a thiol group, an amino group, an alkoxy group, an aryl group, an arylthio group, an aryloxy group, an alkylthio group, a cycloalkyl group, and a heterocyclic group, for example.

In the present description, the halogen atom is, for example, a fluoro atom, a chloro atom, or a bromine atom; the alkyl group is, for example, a straight-chain or branched-chain $C_1$-$C_{30}$ alkyl group such as a methyl group, an ethyl group, a propyl group, an isopropyl group, a butyl group, a pentyl group, a heptyl group, an octyl group, or a pentadecanyl group; the lower alkyl group is, for example, a straight-chain or branched-chain $C_1$-$C_{10}$ alkyl group; the aryl group is, for example, a phenyl group, a naphthyl group; the aralkyl group is, for example, an aryl-lower alkyl group; the cycloalkyl group is, for example, a $C_1$-$C_{10}$ cycloalkyl group such as a cyclooctyl group, an adamanthyl group; and the heterocyclic group is, for example, a pyridyl group, a furyl group, a pyrrolidinyl group, an imidazolyl group, a quinolyl group, or an isoquinolyl group.

Also, in the present invention, the bisphosphonate preferably is accepted pharmaceutically and, for example, can be bisphosphonate that has a bone resorption inhibiting effect and generally is used as a therapeutic agent for osteoporosis. Examples thereof include a zoledronic acid, a salt thereof and/or their hydrate (for example, zoledronate sodium hydrate (ZOMETA™, Novartis Pharma AG.)), a pamidronic acid, a salt thereof and/or their hydrate (for example, pamidronate disodium pentahydrate (AREDIA™, Novartis Pharma AG.)), an alendronic acid, a salt thereof and/or their hydrate (for example, alendronate sodium trihydrate (ONCAST™, Banyu Pharmaceutical Co., Ltd.)), a risedronic acid, a salt thereof and/or their hydrate (for example, risedronate sodium hydrate), an ibandronic acid, a salt thereof and/or their hydrate (for example, ibandronate sodium), an incadronic acid, a salt thereof and/or their hydrate (for example, incadronate disodium), and an etidronic acid, a salt thereof and/or their hydrate (for example, etidronate disodium). Among them, the zoledronic acid, the pamidronic acid, the alendronic acid and their salts and/or their hydrates are preferred.

With regard to the disease antigen used in the present invention, the "disease" mentioned above is not particularly limited but is a cancer, or an infectious disease, for example. The cancer is not particularly limited but may be any cancer, for example, a cancer (including a precancer) that is difficult to treat. The infectious disease is not particularly limited but can be, for example, viral infections such as AIDS, hepatitis B and C, cellular infections, bacterial infections, mycoses or protozoiases. There is no particular limitation on the form of the disease antigen used in the present invention, which can be, for example, a cancer antigenic protein, a cancer antigenic peptide, an infectious disease antigenic protein or an infectious disease antigenic peptide. Further, examples of the above-noted disease antigen include a lysed cancer cell or a lysed infectious disease cell, and an apoptotic cell and a necrotic cell of a cancer cell or an infectious disease cell, and a heat-treated product thereof In the case where the above-noted disease antigen is a cancer antigen, any kind of cancer antigen can be used. For example, it is possible to use a cancer antigen of any of a prostate cancer, a hepatoma and a pancreatic cancer. The above-noted cancer antigen can be, for example, those encoded by the MAGE gene family such as MAGE 1, MAGE 3, GAGE, BAGE and RAGE. Examples of other cancer antigens include a cancer antigen arising from mutations such as p53, K-ras, CDK4 and the bcl-c-abl gene product, a cancer antigen that is over-expressed in cancer cells such as c-erb2 (neu) protein and an oncogenic viral antigen such as the E7 protein of HPV-16. Further, it also is possible to use an oncofetal antigen such as carcinoma embryonic antigen (CEA) or α-fetoprotein (AFP), or a differentiation antigen such as a prostate specific antigen and CD-10 (CALLA antigen), which is expressed in B-cell in leukemias and lymphomas.

The kinds of the infectious disease for the infectious disease antigen are not particularly limited, either. For example, the infectious disease can be an intractable disease among viral infections such as AIDS, hepatitis B and C, Epstein-Barr virus (EBV) infection, or HPV infection. Also, an antigen from parasites such as Plasmodium circumsporozoite protein also can be employed.

Further, in the present invention, a synthetic peptide can be used as the above-described disease antigenic peptide. This reduces the burden on the patient compared with the case of using cancer antigen harvested from patient's own cancer tissues. The above-noted cancer antigenic protein or peptide can be, for example, those listed in Tables 1 to 3 below, which can be procured or synthesized easily by a person having an ordinary skill in the art.

[Table 1]

TABLE 1

| Antigen name | Kind of cancer |
| --- | --- |
| AARS | Placentoma |
| ABL1 | Fibroblastoma |
| ACADVL | Placentoma |
| ACLT7B | Brain tumor |
| ACP2 | Lymphoma |
| ACVR2B | Brain tumor |
| ADPRT | Fibroblastoma |
| ADSL | Brain tumor |
| AF6 | Myeloma |
| AFP | Lung cancer |
| AGPAT2 | Renal cancer |
| AIBP | Renal cancer |
| AIM1 | Hepatoma |
| AKAP9 | Brain tumor |
| ALDA | Fibroblastoma |
| ALDOA | Fibroblastoma |
| ALOX12B | Brain tumor, etc. |
| ALPHA NAC | Brain tumor |
| AMHR2 | Scirrhous carcinoma |
| ANT3 | Brain tumor, lung cancer, etc. |
| ANXA11 | Teratocarcinoma |
| ANXA2 | Various cancers |
| AP1G2 | Hepatoma |
| AP1M1 | Hepatoma |
| AP2M1 | Myeloma |
| AP3D1 | Sarcoma, etc. |
| APC | Colon cancer, etc. |
| APEXL2 | Lung cancer, etc. |
| ARL1 | Urinary bladder cancer |
| ARL6IP | Myeloma |
| ARNTL1 | Brain tumor |
| ASNA1 | Uterine cancer |
| ATF3 | Sarcoma |
| ATIC | Hepatoma |
| ATP5B | Placentoma |
| ATRX | Various cancers |
| BAG5 | Brain tumor |
| BAGE | Melanoma, various cancers |
| BASP1 | Brain tumor |
| BAZ1A | Cervical cancer |
| BAZ2A | Scirrhous carcinoma |
| bcr-abl | Chronic myeloid leukemia |
| BIRC2 | Hepatoma |
| BIRC3 | Hepatoma |
| BMAL2 | Brain tumor |
| BMS1L | Myeloma |
| BMX | Prostate cancer, etc. |
| BRD2 | T lymphoma |
| BTG3 | Uterine cancer |
| C21ORF2 | Lung cancer, etc. |
| CALU | Keratinocytoma |
| CARHSP1 | Placentoma |
| CASP-8 | Squamous cell cancer |
| CCN1 | Brain tumor |
| CCT8 | Myeloma |
| CD43 | Renal cancer |
| CDC27 | Melanoma |
| CDC2L5 | Glioblastoma |
| CDIPT | Scirrhous carcinoma |
| CDK4 | Melanoma |
| CEA | Colon cancer, etc. |
| CENF | Breast cancer |
| CENPB | Uterine cancer |
| CHD3 | Thymoma |
| CKAP1 | Myeloma |
| CLIC6 | Digestive cancer |
| CLK3 | Cervical cancer |
| CLN6 | Lung cancer |
| CNTF | Lung cancer, etc. |
| COG8 | Uterine cancer |
| COPB2 | Lung cancer |
| CORO1A | Brain tumor, etc. |

TABLE 1-continued

| Antigen name | Kind of cancer |
| --- | --- |
| COTL1 | Placentoma, etc. |
| CSDA | Placentoma |
| CTAG1 | Melanoma |
| CTAG2 | Melanoma |
| CTAGE-1 | Scirrhous carcinoma |
| CTNNA1 | Colon cancer, etc. |
| CUL5 | Scirrhous carcinoma |
| DAD1 | Brain tumor |
| DCTN1 | Brain tumor |
| DDX5 | Sarcoma |
| DKFZP434N0735 | Brain tumor |
| DKFZP434P112 | Scirrhous carcinoma |
| DKFZP564C236 | Brain tumor |
| DLG5 | Brain tumor |
| DNAJA1 | Placentoma |
| DNAJA2 | Skin cancer |
| DNAJB1 | Placentoma |
| DSP | Skin cancer |
| DUSP12 | Placentoma |
| DYH1B | Hepatoma |
| EBP | Hepatoma |
| EBV-BMLF1 | B lymphoma, etc. |
| EBV-EBNA-2, 3, 4, 6 | B lymphoma, etc. |
| EDF-1 | Pancreatic cancer |
| EEF1G | Hepatoma, etc. |
| EEF2 | Ovarian cancer |
| EF1D | Skin cancer, etc. |
| EGLN1 | Tonsillar cancer |
| EIF3S6IP | Brain tumor, cervical cancer, etc. |
| EIF4EBP3 | Lymphoma |
| EIF4G2 | Placentoma, etc. |
| ela2 | Acute lymphoblastic leukemia |
| EMS1 | Breast cancer |
| EPHB2 | Stomach cancer, etc. |
| ETV6-AML1 | Acute monocytic leukemia |
| FBLN1 | Brain tumor |
| FBXO7 | Pancreatic cancer |
| FDFT1 | Hepatoma |
| FH | Brain tumor |
| FKSG11 | Breast cancer |
| FNBP3 | Skin cancer |
| FXYD5 | Myeloma |
| GAGE3, 4, 5, 6, 7B | Melanoma, various cancers |
| GCC2 | Lymphoma |
| GDF11 | Brain tumor |
| GLIPR1 | Glioma |
| GNB3 | Brain tumor |
| GNG4 | Brain tumor |
| GOA4 | Stomach cancer |
| GOLGA1 | Cervical cancer, scirrhous carcinoma |
| GOT1 | Hepatoma |
| gp100 | Melanoma |
| GRB7 | Lung cancer, etc. |
| GTF2H2 | Skin cancer, etc. |
| GTF2I | Cervical cancer |
| GUCY2D | Retinal tumor |
| H2AFY | Lung cancer, etc. |
| HC58 | Hepatoma |
| HDAC5 | Colon, rectum cancers, etc. |
| HER2/neu | Breast cancer, ovarian cancer, stomach cancer |
| HKF1 | Brain tumor |
| HMGA2 | Hepatoma |
| HMGN1 | Myeloma |

[Table 2]

TABLE 2

| Antigen name | Kind of cancer |
|---|---|
| HMMR | Breast cancer |
| HNRPAB | Placentoma, etc. |
| HPV16-E6 | Cervical cancer, etc. |
| HPV16-E7 | Cervical cancer, etc. |
| HPV18-E6 | Cervical cancer, etc. |
| HPV18-E7 | Cervical cancer, etc. |
| HRASLS3 | Hepatoma, etc. |
| HSP60 | Hepatoma, uterine cancer |
| HSP90A | Various kinds |
| HSPA4 | Lymphoma |
| HSPCA | Placentoma |
| HSPE1 | Uterine cancer |
| HSPH1 | Myeloid leukemia |
| HTLV-1 tax | Adult T cell leukemia |
| ID4 | Uterine cancer |
| IDH2 | Heart, colon cancer |
| IFI16 | T cell leukemia |
| IGBP1 | B lymphoma, etc. |
| IKBKAP | Cervical cancer |
| ILF3 | T lymphocytoma, cervical cancer |
| INPP1 | Colon cancer |
| JPHL1 | Myeloma |
| JUN | Various cancers |
| KCNAB3 | Brain tumor |
| KIAA0117 | Myeloma, lung cancer |
| KIAA0175 | Myeloid leukemia |
| KIAA0291 | Brain tumor, etc. |
| KIAA0570 | Brain tumor |
| KIAA0619 | Brain tumor |
| KIAA0801 | Brain tumor |
| KIAA0909 | Brain tumor |
| KIAA0975 | Brain tumor |
| KIAA0989 | Brain tumor |
| KIF22 | Lymphoblastoma |
| KIF9 | Scirrhous carcinoma, etc. |
| KLHL2 | Brain tumor |
| KNS2 | Brain tumor, etc. |
| KRT13 | Pancreatic cancer |
| KRT14 | Pancreatic cancer |
| KRT18 | Cervical cancer |
| KRT7 | Placentoma |
| KRT8 | Colon cancer, etc. |
| KTN1 | Lymphoma |
| LB1 | B lymphoma, etc. |
| LDHA | Sarcoma |
| LDHB | Urinary bladder cancer, sarcoma, etc. |
| LGALS1 | Lung cancer |
| LGALS4 | Stomach cancer |
| LIMS1 | Myeloma |
| LMNA | Lung cancer, renal cancer |
| LRP130 | Hepatoma |
| LYST | Lung cancer, etc. |
| MAGE-1 | Melanoma, various cancers |
| MAGE-2 | Melanoma, various cancers |
| MAGE-3 | Melanoma, various cancers |
| MAGE-4 | Melanoma, various cancers |
| MAGE-6 | Melanoma, various cancers |
| MAGED2 | Breast cancer, various cancers |
| MAN2C1 | Scirrhous carcinoma, etc. |
| MAP1B | Brain tumor |
| MAPK1 | Lung cancer, etc. |
| MARK4 | Brain tumor |
| MART-1 | Melanoma |
| MAZ | Pancreatic cancer, etc. |
| MBD2 | Lymphoma |
| MCM3 | Cervical cancer, pancreatic cancer |
| MED6 | Lung cancer, etc. |
| MESDC2 | Myeloma |
| MIF | Brain tumor, etc. |
| MJD1 | Brain tumor |
| MK167 | Various cancers |
| MLF1 | Urinary bladder cancer, etc. |

TABLE 2-continued

| Antigen name | Kind of cancer |
|---|---|
| MLH1 | Pancreatic cancer, urinary bladder cancer |
| MRPS26 | Skin cancer |
| MSLN | Uterine cancer |
| MUC-1 mucin | Breast cancer, ovarian cancer, pancreatic cancer, etc. |
| MUM-1 | Melanoma |
| MVP | Retinal tumor |
| MYH10 | Sarcoma |
| MYH9 | Myeloma |
| MYO9B | Hepatoma |
| NAF1 | Lymphoma |
| NAP | Scirrhous carcinoma |
| NAP1L1 | Melanoma |
| NASP | Scirrhous carcinoma |
| NBC4 | Scirrhous carcinoma |
| NCOR2 | Brain tumor |
| NDUFV3 | Brain tumor |
| NEDD9 | Lymphoma |
| NFE2L2 | Melanoma |
| NME1 | Lung cancer, etc. |
| NME2 | Retinal tumor |
| NOTCH2 | Breast cancer, etc. |
| NRIP1 | Breast cancer |
| NUDT4 | Placentoma |
| NUPL1 | Brain tumor, placentoma |
| NY-CO-10 | Colon, rectum cancers |
| NY-CO-33 | Colon cancer |
| NY-CO-7 | Colon, rectum cancers |
| NY-CO-8 | Colon, rectum cancers |
| NY-ESO-1 | Scirrhous carcinoma |
| OCLN | Colon cancer |
| OGFR | Skin cancer, etc. |
| p53 | Squamous cell carcinoma, etc. |
| PAD3 | Renal cancer |
| PAF1 | Hepatoma |
| PAP | Prostate cancer |
| PDAP1 | Various cancers |
| PDI | Colon cancer, lung cancer, etc. |
| PDXK | Ovarian cancer |
| PECI | Hepatoma |
| PFAS | Brain tumor |
| PFKFB3 | Brain tumor, etc. |
| PFN1 | Colon, lung, pancreatic cancers |
| PFN2 | Brain tumor |
| PHF11 | Erythroblastoma |
| PHF3 | Glioma, etc. |
| PHKG2 | Hepatoma, etc. |
| PI3 | Skin cancer |
| PIAS1 | B cellular leukemia |
| PICALM | Myeloma |
| PKCB1 | T cell tumor |
| PKD1 | Renal cancer |
| PMSCL1 | Lymphoblastoma |
| POLR2E | Lung cancer |
| PPM1B | Hepatoma |
| PPP2R5C | Myeloma, etc. |
| PPP4C | Placentoma, myeloma |
| PRC1 | Renal cancer |
| PRDM5 | Various cancers |
| PRDX1 | Urinary bladder cancer |
| PRKWNK2 | Colon cancer |
| proteinase3 | Acute myeloid leukemia |
| PSA | Prostate cancer |
| PSMD4 | Brain tumor |

[Table 3]

TABLE 3

| Antigen name | Kind of cancer |
|---|---|
| PSMD9 | Sarcoma |
| PSME3 | Lung cancer, etc. |
| PTMS | Renal cancer |

TABLE 3-continued

| Antigen name | Kind of cancer |
|---|---|
| PTTG | Brain tumor |
| QPRT | Brain tumor, brain, renal sarcomas, etc. |
| RAB5C | Lung cancer, etc. |
| RAGE | Renal cancer |
| RAN | Brain tumor |
| ras | Pancreatic cancer, colon cancer, hepatoma, etc. |
| RASSF1 | Pancreatic cancer |
| RBM10 | Lung cancer, myeloma |
| RBM6 | Lung cancer |
| RGS19IP1 | Lung cancer, etc. |
| RNF12 | Renal cancer |
| RNPC2 | Hepatoma |
| RPA2 | Renal cancer, etc. |
| RPL10 | Breast cancer |
| RPL10A | Skin cancer |
| RPL21 | Colon cancer |
| RPL27A | Colon cancer |
| RPL3 | Colon cancer |
| RPL30 | Breast cancer |
| RPL32 | Renal cancer |
| RPL34 | Uterine cancer |
| RPL37A | Brain tumor |
| RPS15A | Colon cancer |
| RPS18 | Placentoma |
| RSN | Monocytic leukemia |
| RUVBL1 | Colon, rectum cancers |
| SART-1 | Various cancers |
| SATB1 | Lung cancer |
| SBDS | Uterine cancer |
| SCNN1A | Renal cancer, etc. |
| SCP1 | Scirrhous carcinoma |
| SCP2 | Hepatoma |
| SCR3 | Lung cancer |
| SDBCAG84 | Breast cancer |
| SEC14L1 | Lung cancer, etc. |
| 1-Sep | Breast cancer |
| SFRS5 | Colon cancer |
| SGPL1 | Brain tumor |
| SIN3A | Brain tumor |
| SK-Br-3 | Breast cancer |
| SLC22A17 | Brain tumor |
| SLC25A11 | Brain tumor |
| SLC25A2 | Scirrhous carcinoma |
| SLC25A27 | Brain tumor |
| SLX13 | Brain tumor |
| SMTN | Colon cancer |
| SNN | Brain tumor |
| SNT-1 | Uterine cancer |
| SNX6 | Various cancers |
| SOX1 | Brain tumor |
| SOX2 | Brain tumor |
| SPN | Renal cancer, etc. |
| SR+89 | Lung cancer |
| SRP19 | Hepatoma, etc. |
| SSA1 | Thymoma, etc. |
| SSA2 | Skin cancer |
| SSNA1 | Scirrhous carcinoma |
| SSP1 | Hepatoma, etc. |
| SSSCA1 | Uterine cancer |
| SSX1 | Fibroblastoma |
| SSX4 | Urinary bladder cancer, etc. |
| ST13 | Colon cancer |
| STARD10 | Colon cancer |
| STARD7 | Uterine cancer, etc. |
| STIP1 | Lung cancer |
| STK11 | Hepatoma, etc. |
| STM | Brain tumor |
| STX4A | Various cancers |
| SUCLA2 | Hepatoma, etc. |
| SULT1A3 | Brain tumor, etc. |
| SURF5 | Lung cancer, skin cancer, etc. |
| SYCP1 | Scirrhous carcinoma |
| TADA3L | Various cancers |
| TAF10 | Hepatoma, etc. |
| TAF7 | Skin cancer |
| TBC1D1 | Brain tumor, etc. |
| TBC1D4 | Brain tumor |
| TBC1D5 | Myeloma |
| TCE1 | Renal cancer |
| TCEB3 | Lung cancer |
| TCF4 | Thymoma |
| TDRD3 | Placentoma |
| TEL-AML1 | Acute monocytic leukemia |
| TGFBI | Renal cancer |
| TIAF1 | Breast cancer |
| TIMP3 | Renal cancer |
| TKT | Hepatoma |
| TMF1 | Cervical cancer, pancreatic cancer |
| TNKS2 | Breast cancer |
| TNNT1 | Sarcoma |
| TOP2B | Various cancers |
| TP53BP2 | Various cancers |
| TPD52 | Breast cancer |
| TPI1 | Hepatoma |
| TPM1 | Hepatoma |
| TRAPPC1 | Uterine cancer |
| TRP1, 2 | Melanoma |
| TSTA3 | Lung cancer |
| TTC12 | Lymphoma |
| TXNRD1 | Pancreatic cancer, etc. |
| tyrosinase | Melanoma |
| U2AF1L1 | Brain tumor |
| U2AF1L2 | Brain tumor |
| UBE1 | Placentoma |
| UBE2D2 | Scirrhous carcinoma |
| UBQLN2 | Lung cancer |
| UE3A | Keratinocytoma |
| UN1 | Breast cancer, lung cancer, stomach cancer, etc. |
| USH1C | Colon cancer |
| USP1 | Scirrhous carcinoma |
| USP10 | Myeloma |
| USP16 | Scirrhous carcinoma |
| USP19 | Brain tumor |
| USP32 | Brain tumor |
| USP4 | Brain tumor |
| VCL | Uterine cancer |
| VEGFB | Fibroblastoma |
| VESPR | Skin cancer |
| VPS45A | Brain tumor |
| WT1 | Various leukemia, various cancers |
| YARS | Lung cancer, etc. |
| YWHAE | Hepatoma, etc. |
| ZFP36L2 | T cell leukemia |
| ZIC2 | Brain tumor |
| ZNF202 | Scirrhous carcinoma |
| ZNF232 | Erythroblast |
| ZNF282 | T lymphocytic leukemia |
| ZNF292 | Placentoma |
| β-catenin | Melanoma |
| Antibody idiotype | B lymphoma |

In the present invention, pulsing an antigen-presenting cell with a certain substance means to cause the antigen-presenting cell to react with that substance and preferably means to present the above-noted substance directly or indirectly on a surface of the antigen-presenting cell. Also, co-pulsing an antigen-presenting cell means to pulse the antigen-presenting cell with at least two substances simultaneously, successively or intermittently. The above-mentioned substance preferably is bisphosphonate and/or a disease antigen.

Now, the method for activation treatment of an antigen-presenting cell according to the present invention and the method for producing an activated antigen-presenting cell according to the present invention will be detailed with reference to the following example using a dendritic cell as the antigen-presenting cell. In the present invention, the activation treatment of an antigen-presenting cell refers to a process including co-pulsing an antigen-presenting cell with bisphosphonate and a disease antigen, as described above.

First, the preparation of antigen-presenting cells (dendritic cells in this example) will be explained. The preparation of the dendritic cells starts with acquiring a sample for obtaining precursors of the dendritic cells. The above-noted sample can be peripheral blood, bone marrow, umbilical cord blood or the like. The peripheral blood is used preferably in light of the fact that it is easily available and does not put much burden on a patient. It is preferable that the amount of blood to be collected is determined so that it causes no burden on a donor. The method for collecting the blood can be whole blood collection using a vacuum blood collection tube, a blood collection bag or the like. Also, when a large amount of cells is needed, it is possible to obtain peripheral blood mononuclear cells directly by employing a method of collecting a mononuclear cell fraction using an apheresis instrument. In order to avoid coagulation, heparin or a citric acid may be added to the collected blood.

Next, mononuclear cells containing the precursors of the dendritic cells are separated from the collected blood. The separation can be carried out by any method of separating nuclear cells from erythrocytes. For example, a method utilizing Ficoll fractionation, i.e., Ficoll-Paque density gradient or elution is employed generally. It is preferable that the collected cells are washed several times using a culture medium, a physiological saline solution, or a phosphate buffered saline (hereinafter, referred to as PBS) for the purpose of removing thrombocytes.

Subsequently, monocytes (CD14-positive cells), which are the precursors of the dendritic cells, are separated from the collected mononuclear cells. CD14 is known as a marker that is expressed in monocytes, which are the precursors of the dendritic cells. Thus, the monocytes can be isolated and collected with Magnetic Cell Sorting (Miltenyi Biotec; hereinafter, referred to as MACS) using anti-CD14 antibody magnetic beads. This method is preferable because of its simplicity and higher recovery of monocyte. Alternatively, it also may be possible to employ a method including transferring the collected mononuclear cells to a culture flask, culturing them at 34° C. to 38° C., more preferably 37° C., under a condition of 2% to 10% $CO_2$, more preferably 5% $CO_2$, for at least one hour, and using adherent cells as the precursors of the dendritic cells.

Thereafter, differentiation induction of immature dendritic cells or mature dendritic cells from the obtained precursors of the dendritic cells is carried out. As the culture medium, an AIM-V medium (Invitrogen Corporation) is used. Other than the AIM-V medium, it is possible to use a commercially available medium that is used for cell culture, such as an RPMI-1640 medium (Invitrogen Corporation), Dulbecco's Modified Eagle Medium (Invitrogen Corporation; hereinafter, referred to as DMEM), TIL (Immuno-Biological Laboratories Co., Ltd.), an epidermal keratinocyte medium (Kohjin Bio Co., Ltd.; hereinafter, referred to as KBM) or Iscove's medium (Invitrogen Corporation; hereinafter, referred to as IMEM). Further, it is possible to add 0.5% to 20% bovine serum, fetal bovine serum (hereinafter, referred to as FBS), human serum, human plasma or the like, as necessary.

In the case of obtaining the immature dendritic cells, a differentiation inducer is added to the culture medium so as to culture the precursors of the dendritic cells. The differentiation inducer can be any cytokines. For example, a granulocyte macrophage colony stimulating factor (hereinafter, referred to as GM-CSF), interleukin 4 (hereinafter, referred to as IL-4; other interleukins also are referred to in a similar manner), a stem cell factor (hereinafter, referred to as SCF), IL-13, or a tumor necrosis factor α (hereinafter, referred to as TNF-α) can induce the immature dendritic cells efficiently. Further, it is preferable to add IL-1, IL-2, or IL-3, as necessary. More preferably, the use of GM-CSF and IL-4 in combination allows an efficient induction. The culture is conducted at 34° C. to 38° C., preferably 37° C., under a condition of 2% to 10% $CO_2$, preferably 5% $CO_2$, and the culture period preferably is 5 to 7 days.

In the case of obtaining the mature dendritic cells, a further differentiation inducer is added on day 5 to day 7 after starting culture, followed by further culturing. The differentiation inducer can be any cytokines. For example, it is preferable to induce the mature dendritic cells efficiently using GM-CSF, IL-4, SCF, IL-1β, IL-6, IL-13, TNF-α, or prostaglandin $E_2$ (hereinafter, referred to as $PGE_2$). Further, it is preferable to add IL-1, IL-2, or IL-3, as necessary. More preferably, the use of GM-CSF, IL-4, IL-6, IL-1, $PGE_2$ and TNF-α in combination allows an efficient induction. The culture is conducted at 34° C. to 38° C., preferably 37° C., under a condition of 2% to 10% $CO_2$, preferably 5% $CO_2$, and the culturing time preferably is 24 to 48 hours.

Moreover, it also is possible to use a method including collecting hematopoietic stem cells (CD34-positive cells) as the precursors of the dendritic cells and adding thereto GM-CSF, TNF-α and flt-3 ligand (FL), c-kit ligand (SCF) or thrombopoietin (TPO) solely or in combination, thus obtaining the immature dendritic cells or the mature dendritic cells, or a method including collecting dendritic cell fraction directly from blood or separated peripheral blood mononuclear cells using a density gradient solution such as Percoll.

Next, the resultant antigen-presenting cells (in this example, the immature dendritic cells or the mature dendritic cells) are co-pulsed with bisphosphonate and a disease antigen.

The concentration of bisphosphonate is not particularly limited as long as it is the concentration in which cells usually are pulsed with bisphosphonate. For example, 0.001 to 20 µM are preferable, and 0.001 to 5 µM are further preferable, as described in a document [The Journal of Immunology, 2001, Vol. 166, 5508-5514 or Blood, 2001, Vol. 98, No. 5, 1616-1618].

The concentration of the disease antigen is not particularly limited as long as it is the concentration in which dendritic cells usually are pulsed with a disease antigen. For example, in the case of the disease antigenic protein or peptide described above, 0.01 to 20 µg/ml are preferable, and 0.1 to 2 µg/ml are further preferable, as described in a document [Cancer Research, 1999, Vol. 59, 2167-2173, The Journal of Immunology, 1995, Vol. 154, 2257-2265 or The Journal of Immunology, 1994, 153, 996-1003].

Further, in the case of pulsing the dendritic cells with a cell population including the apoptotic cell and/or the necrotic cell as the disease antigen, examples of the method for preparing the above-noted cell population can include 1) a method of culturing a cancer cell or a cancer cell line so as to allow spontaneous formation of a cell population, 2) a method of subjecting a cancer cell or a cancer cell line to UV irradiation (1 $J/cm^2 \cdot sec$ for 2 minutes) so as to cause the cell population formation and 3) a method of heat-treating a cancer cell or a cancer cell line at 85° C. for 10 minutes so as to cause the cell population formation.

The activated antigen-presenting cells of the present invention (in this example, the activated dendritic cells) prepared (produced) by the above-described method for activation treatment according to the present invention can induce efficiently immunocytes that dominantly include disease antigen-specific CD8+ CTLs and/or γδ T cells. For example, in the case of either in vitro or in vivo, the activated antigen-presenting cells of the present invention can be used as a medical composition capable of inducing immunocytes that dominantly include disease antigen-specific CTLs and/or γδ T cells. In particular, such a medical composition preferably is used as treatment and prevention agents for cancer and/or infectious disease. In the present invention, the immunocytes refer to cells capable of recognizing the specificity of an antigen and/or being involved in a specific immune reaction including T cells, iNKT cells, NK cells (Natural Killer Cells), B cells, monocytes, dendritic cells and macrophages, or a cell population including one kind or two or more kinds of these cells. Also, in the present invention, dominantly including disease antigen-specific CD8+ CTLs and/or γδ T cells means that the ratio and/or the number of the disease antigen-specific CD8+ CTLs and/or γδ T cells increase compared with those before stimulation. In the case where the activated antigen-presenting cells of the present invention are used in vitro, they can be used as a composition capable of inducing the immunocytes that dominantly include disease antigen-specific CD8+ CTLs and/or γδ T cells. In the case where the activated antigen-presenting cells of the present invention are used in vivo, they can be used as a vaccine such as a dendritic cell vaccine capable of inducing the immunocytes that dominantly include disease antigen-specific CD8+ CTLs and/or γδ T cells after free bisphosphonate and a disease antigen are removed by washing. Additionally, in both the cases of using the activated antigen-presenting cells of the present invention in vitro and in vivo, cytokines (for example, IL-2) and other proteins (for example albumin), etc., for example, also may be used, as necessary.

Embodiment 2

Medical Composition Comprising Activated Antigen-Presenting Cells of the Present Invention Now, a medical composition using activated antigen-presenting cells of the present invention will be described by way of an example using dendritic cells as the antigen-presenting cells similarly to the above.

First, the activated antigen-presenting cells (the activated dendritic cells) obtained in Embodiment 1 described above are collected by a centrifugation. Next, the collected cells are washed. A liquid used for washing can be any liquid as long as it is isotonic and can be used as pharmaceutical preparations. Considering later administration to a patient, it is preferable to use a physiological saline solution, PBS or the like. Then, the collected dendritic cells are suspended in a physiological saline solution and become applicable as a medical composition. It also is possible to add a serum component such as albumin and cytokines, as necessary. In particular, such a medical composition preferably is used as treatment and prevention agents for cancer and/or infectious disease. Accordingly, as a related embodiment, the present invention includes the use of the activated antigen-presenting cell of the present invention for producing a medical composition for a cancer and/or an infectious disease.

Embodiment 3

Treatment and Prevention Method Using Activated Antigen-Presenting Cells of the Present Invention Now, a treatment and prevention method using dendritic cells of the present invention will be described by way of an example using dendritic cells as the antigen-presenting cells similarly to the above.

By administering the activated antigen-presenting cells (the activated dendritic cells) of the present invention obtained in Embodiment 1 or the medical composition of the present invention obtained in Embodiment 2 described above, it is possible to treat and prevent a cancer and/or an infectious disease.

The number of cells to be administered can be selected suitably according to an administration method and a patient's condition, without any particular limitation. For example, at one time, $10^6$ to $10^8$ cells per person preferably are administered, and at least $10^7$ cells per person more preferably are administered. The number of administrations varies according to the patient's condition and may be 4 to 6 times as one course. The interval of administrations depends on the number of the dendritic cells to be administered and is not particularly limited. It is preferable to administer the dendritic cells once a week to once a month. Further, it is preferable to administer the dendritic cells every two weeks if the number of the cells is $5 \times 10^6$, and it is preferable to administer them once a month if the number is $2 \times 10^7$ or greater. The method for administration is not particularly limited but can be intravenous injection, hypodermic injection, intracutaneous injection, direct injection to a regional lymph node, direct injection to a lesioned site, or systemic administration by dripping. Alternatively, it also is possible to inject the dendritic cells from an artery near the lesioned site.

By administering the activated antigen-presenting cells of the present invention in this manner, it is possible to activate and proliferate not only the disease antigen-specific CD8+ CTLs but also the γδ T cells in the patient's body.

These disease antigen-specific CTLs and/or the γδ T cells not only can kill a cancer cell and an infected cell directly but also injure these cells indirectly via cytokines such as interferon γ (hereinafter, referred to as IFNγ). Therefore, they can be used effectively for various treatment and prevention of cancers and infectious diseases, for example. The advantage of using the activated antigen-presenting cells of the present invention as a vaccine follows. A conventional vaccine of dendritic cells pulsed with a disease antigen alone activates only disease antigen-specific CD8+ CTLs. In contrast, the vaccine of the activated antigen-presenting cells of the present invention can activate γδ T cells in addition to disease antigen-specific CD8+ CTLs. Furthermore, cytokines that are induced from these disease antigen-specific CD8+ CTLs and/or γδ T cells are capable of activating a helper T cell, an NK cell, an iNKT cell (invariant Natural Killer T Cell) and a B cell. This activates a humoral and a cellular immunity in an entire organism, so that the effect of treatment and prevention improves. Also, the antigen-presenting cells used for the activation treatment preferably are autologous antigen-presenting cells of the patient or allogeneic antigen-presenting cells that share the same HLA. This is because, when they are administered to the patient, their function can be exhibited without being removed by the patient's immunity.

Embodiment 4

Method for Inducing Immunocytes that Dominantly Include Disease Antigen-Specific CD8+ CTLs and/or γδ T Cells Now, a method for inducing immunocytes according to the present invention will be described. The method for inducing immunocytes according to the present invention is a method for inducing immunocytes that dominantly include disease antigen-specific CD8+ CTLs and/or γδ T cells, and more specifically, an induction method including a process (i) of co-pulsing an antigen-presenting cell with bisphosphonate and a disease antigen, and a process (ii) of co-culturing the antigen-presenting cell and a lymphocyte simultaneously with or after the co-pulse. Here, the immunocyte refers to a cell capable of recognizing the specificity of an antigen and/or being involved in a specific immune reaction, including a T cell, an iNKT cell, an NK cell, a B cell, a monocyte, a dendritic cell and a macrophage, or a cell population including one kind or two or more kinds of these cells, as described above.

First, an activation treatment of antigen-presenting cells (for example, dendritic cells) is carried out similarly to Embodiment 1 (the process (i)). Then, simultaneously with or after the co-pulse, the antigen-presenting cells and responding cells are added into a culture container for co-culturing (the process (ii)). In this way, in response to a disease antigen-specific stimulation from the antigen-presenting cells that have been subjected to the activation treatment, the disease antigen-specific CD8+ CTLs in the responding cells could be activated. Further, in response to stimulation from IPP (Isopentenyl diphosphate) like molecules that are presented on the surface of the antigen-presenting cells by the inhibition of an antigen-presenting cell metabolic system caused by the bisphosphonate pulse, the γδ T cells in the responding cells could be activated. IFNγ produced from the γδ T cells is capable of assisting further activation and proliferation of the disease antigen-specific CD8+ CTLs. Incidentally, the responding cells here are, for example, human lymphocytes and preferably are monocytes derived from peripheral blood. These responding cells preferably are autologous responding cells or allogeneic responding cells that share the same HLA.

The above-mentioned culture container is not particularly limited and usually can be a culture plate, a laboratory dish, a flask, a bag or the like used in the art. The concentration in which each cell population is added can be set freely according to the situation.

In the case where the antigen-presenting cells are dendritic cells, the dendritic cells and the responding cells can be co-cultured using an AIM-V medium, for example. Other than the AIM-V medium, it is possible to use a commercially available medium that is used for cell culture, such as an RPMI-1640 medium, DMEM, TIL, KBM or IMEM. Further, 5% to 20% serum such as bovine serum, FBS, human plasma, or cytokine or the like may be added, as necessary. The culturing is carried out at, for example, 34° C. to 38° C., preferably 37° C., under a condition of, for example, 2% to 10% $CO_2$, preferably 5% $CO_2$. The culturing period is not particularly limited and preferably is 5 to 21 days and further preferably is 7 to 14 days. The number of the dendritic cells and the responding cells to be added can be set according to a container that is used and an intended use. Also, the mixture ratio between the dendritic cells and the responding cells can be set suitably according to the situation, without any particular limitation. For the purpose of increasing the ratio of the disease antigen-specific CD8+ CTLs and/or the γδ T cells in the responding cells, it is preferable that the ratio of the responding cells to the dendritic cells is 20:1 to 2:1.

With the above-described induction method of the present invention, it is possible to prepare (produce) the immunocytes of the present invention that dominantly include the disease antigen-specific CD8+ CTLs and/or the γδ T cells. Also, the thus obtained immunocytes of the present invention can be used as they are or after repeated stimulations with the activated antigen-presenting cells of the present invention as immunocytes that include the disease antigen-specific CD8+ CTLs and/or the γδ T cells at a higher ratio in an immuno-cell therapy. Accordingly, enhanced effect of treating and preventing cancer and infectious disease can be expected.

The advantage of preparing the immunocytes of the present invention in vitro follows. By stimulating the responding cells repeatedly with the activated antigen-presenting cells of the present invention, it is possible to prepare a large amount of immunocytes capable of directly killing cancer cells and infectious disease cells in a simplified manner.

Embodiment 5

Medical Composition Comprising Immunocytes of the Present Invention

Now, a medical composition comprising immunocytes of the present invention will be described.

First, the immunocytes of the present invention that dominantly include the disease antigen-specific CD8+ CTLs and/or the γδ T cells obtained in Embodiment 4 described above are collected by a centrifugation. Next, the collected cells are washed. A liquid used for washing can be any liquid as long as it is isotonic and can be used as pharmaceutical preparations. Considering later administration to a patient, it is preferable to use a physiological saline solution, PBS or the like. Then, the collected immunocytes that dominantly include the disease antigen-specific CD8+ CTLs and/or the γδ T cells are suspended in a physiological saline solution and become applicable as a medical composition. It also is possible to add cytokines, as necessary. In particular, such a medical composition preferably is used as treatment and prevention agents for cancer and/or infectious disease. Accordingly, as a related embodiment, the present invention includes the use of the activated antigen-presenting cell of the present invention for producing a medical composition for a cancer and/or an infectious disease.

Embodiment 6

Treatment and Prevention Method Using Immunocytes of the Present Invention

Now, a treatment and prevention method using immunocytes of the present invention will be described.

By administering the immunocytes of the present invention obtained in Embodiment 4 or the medical composition of the present invention obtained in Embodiment 5 described above, it is possible to treat and prevent a cancer and/or an infectious disease.

The number of immunocytes to be administered can be selected suitably according to an administration method and a patient's condition, without any particular limitation. For example, at one time, $10^8$ to $10^{12}$ immunocytes per person preferably are administered, and at least $10^9$ immunocytes per person more preferably are administered. The number of administrations varies according to the patient's condition and usually is 4 to 6 times as one course. The interval of administrations is not particularly limited, and it is preferable to administer the immunocytes every two weeks or once a month, for example. The method for administration is not particularly limited but can be intravenous injection, hypodermic injection, intracutaneous injection, direct injection to a regional lymph node, direct injection to a lesioned site, or systemic administration by dripping. Alternatively, it also is possible to inject the immunocytes from an artery near the lesioned site. Also, the immunocytes of the present invention preferably are autologous immunocytes of the patient or allogeneic immunocytes that share the same HLA. This is because, when they are administered to the patient, their function can be exhibited without being rejected by the patient's immune system.

Embodiment 7

Activation Accelerator of Antigen-Presenting Cells at the Time of Pulse with Disease Antigen Now, an activation accelerator of antigen-presenting cells at the time of pulse with disease antigen of the present invention will be described.

The activation accelerator of antigen-presenting cells at the time of pulse with the disease antigen of the present invention contains bisphosphonate as an effective component. The above-noted activation accelerator further may contain a vehicle and/or a carrier that are pharmaceutically acceptable. The above-noted activation accelerator can be added at the time of pulsing the antigen-presenting cells with the disease antigen in vivo and/or in vitro, namely, before, simultaneously with and/or after the pulse with the disease antigen. The other aspects of the present invention include a use of bisphosphonate for producing the activation accelerator of antigen-presenting cells at the time of pulse with the disease antigen. Further, the other modes of the present invention include a treatment and prevention method of cancer and/or infectious disease using bisphosphonate.

The following is a detailed description of the present invention by way of examples. It is needless to say that the present invention is by no means limited to these examples.

Example 1

Example 1-1

Harvest and Preparation of Dendritic Cells

From a healthy donor (HLA-A*0201), 30 ml of peripheral blood was collected. Mononuclear cells were obtained from this peripheral blood of the healthy donor. At this time, a mononuclear cell layer was collected using a density gradient solution for blood cell separation. In order to remove platelets and other components, the collected cells were washed several times in AIM-V to which 10% FBS had been added, and then CD14-positive cells were isolated as monocytes with MACS.

From the obtained dendritic cell precursors, differentiation induction of dendritic cells was carried out. The medium was prepared by adding 500 U/ml of GM-CS F (IMMUNEX) and 500 U/ml of IL-4 (Osteogenetics GmbH) to AIM-V to which 10% FBS or AB serum had been added. On day 5 to day 7 after starting culture, immature dendritic cells were obtained.

Furthermore, on day 5 to day 7 after starting culture, 100 U/ml or 10 ng/ml of IL-6 (R&D systems), 10 ng/ml of IL-1β (CHEMICON), 10 ng/ml of TNFα (PHARMINGEN) and 1 μg/ml of PGE$_2$ (SIGMA) were added, followed by further culturing, thus obtaining mature dendritic cells after 24 to 48 hours.

Example 1-2

Confirmation of State of Dendritic Cells

A surface antigen of the prepared dendritic cells was detected using a flow cytometer (EPICS XL-MCL; Beckman Coulter).

A target antibody was added to a PBS suspension of cells to be measured, thus dyeing the cells in a shielded state at 4° C. for 15 minutes. The antibody was an anti-CD14 antibody, an anti-CD83 antibody or an anti-HLA-DR antibody that was labeled with PE (Beckman Coulter). As a negative control, an isotype of each of the antibodies was used. After the dyed cells were washed in PBS, they were measured with EPICS XL.MCL.

The results showed that the cells cultured with GM-CSF and IL-4 were CD14 negative, CD83 negative and HLA-DR positive. Thus, they were confirmed to be immature dendritic cell population. Also, the cells cultured with GM-CSF, IL-4, IL-6, IL-1β, TNFα and PGE$_2$ were positive except for CD14. Thus, they were confirmed to be mature dendritic cell population.

Example 1-3

Preparation of Dendritic Cells Co-Pulsed with ZOMETA™ and Disease Antigenic Peptides and Preparation of Responding Cells To a suspension of the immature dendritic cells or the mature dendritic cells derived from peripheral blood prepared as described above, ZOMETA™ (Novartis), which was an aminobisphosphonate agent, was added as a zoledronic acid so as to achieve 0.01 μM, and/or MART-1 antigenic peptides A27L (ELAGIGILTV) (hereinafter, referred to as A27L) were added as disease antigenic peptides so as to achieve a final concentration of 2 μg/ml, followed by culturing at 37° C. under a condition of 5% CO$_2$ for about 12 hours. As a negative control, dendritic cells that were cultured without adding ZOMETA™ or the antigenic peptides were used.

After about 12 hours of culture, part of the activated dendritic cells that were co-pulsed with ZOMETA™ and the antigenic peptides were collected, placed in a 15 ml tube (BD Falcon) and centrifuged at 1500 rpm for 5 minutes. The resultant dendritic cells in the form of pellets were suspended in 10 ml of an AIM-V medium supplemented with 10% FBS and centrifuged at 1500 rpm for 5 minutes, followed by washing. The washing operation was repeated twice. The dendritic cells collected in this manner were used as stimulating cells. In other words, the activated dendritic cells that were co-pulsed with bisphosphonate and the disease antigenic peptides, the dendritic cells that were pulsed with either of them and the dendritic cells that were not pulsed with any of them were used as stimulating cells. Cells prepared by suspending those (a CD14-negative cell population, which was mainly a T cell population) remaining after isolation of the CD14-positive cells for preparing the dendritic cells in an AIM-V medium supplemented with 10% FBS and 10% dimethyl sulfoxide (DMSO), and freeze-preserving them were thawed, washed and used as responding cells.

Example 1-4

Characterization of Immunocytes Induced from Dendritic Cells Co-Pulsed with ZOMETA™ and Disease Antigenic Peptides 2×10$^5$ each of the stimulating cells (dendritic cells) obtained as described above were cultured with 2×10$^6$ responding cells such that the total amount was 1 ml in a 24-well plate (SUMILON) (responding cells:dendritic cells=10:1). The culture was carried out at about 37° C. under a condition of 5% CO$_2$ for 7 days. When 20 U/ml of IL-2 was added to this co-cultured solution, the cells were proliferated more favorably. In the case where the cells were proliferated rapidly, 1 ml of an AIM-V medium supplemented with 40 U/ml of IL-2 and 10% FBS was added on day 4 to day 6. Then, 7 days after the start of the co-culture of the dendritic cells and the responding cells, the ratio of the A27L-specific CD8+ CTLs (the disease antigen-specific CD8+ CTLs) in all of the cells was measured with a flow cytometer using a labeled antibody and an antigen-specific tetramer.

The procedure of calculating the ratio of HLA-A*0201 A27L tetramer-positive and CD8-positive cells is as follows: first, A27L tetramer that was labeled with PE (MBL) was added to the cells that had been washed in PBS after cultured. After dyeing in a shielded state at room temperature for 15 minutes, an anti-CD8 antibody that was labeled with FITC (BD Pharmingen) was added, followed by dyeing in a shielded state at 4° C. for 15 minutes. As a control, an isotype of each of the antibodies was used. The cells were measured using EPICS XL.MCL, and the results of measurement were analyzed using EPICS 32.

The results are shown in Table 4a below. As shown in this table, it was confirmed that the activated dendritic cells that were co-pulsed with 0.01 μM of ZOMETA™ and 2 μg/ml of A27L induced the antigen-specific CD8+ CTLs. Further, the ratio of the antigen-specific CD8+ CTLs in the case of using these activated dendritic cells was confirmed to be about 4 times as high as that of CTLs induced from dendritic cells that were pulsed with peptides alone.

Moreover, Table 4b and FIG. 1 show the results of a t-test when a similar experiment was conducted with a larger number of subjects. It became clear that the ratio of the CD8+ CTLs obtained using the dendritic cells that were co-pulsed with A27L and ZOMETA™ was higher than that of the CD8+ CTLs obtained using the dendritic cells that were pulsed with A27L alone, with a significant difference existing therebetween.

[Table 4]

TABLE 4a

Ratio (%) of disease antigen-specific CD8+ CTLs induced by culturing activated immature dendritic cells pulsed using ZOMETA ™ and/or A27L and lymphocytes

| Sample used for pulsing dendritic cells | | |
|---|---|---|
| A27L | ZOMETA ™ | A27L + ZOMETA ™ |
| 0.09 | 0.00 | 0.39 |

TABLE 4b

Ratio (%) of disease antigen-specific CD8+ CTLs induced by culturing activated immature dendritic cells pulsed using ZOMETA ™ and/or A27L and lymphocytes

| | Sample used for pulsing dendritic cells | | |
|---|---|---|---|
| Donor | A27L | A27L + ZOMETA ™ | Scale factor |
| 01 | 0.05 | 0.38 | 7.60 |
| 02 | 0.09 | 0.61 | 6.78 |
| 03 | 0.07 | 0.40 | 5.71 |
| 04 | 1.02 | 2.66 | 2.61 |
| 05 | 0.22 | 0.94 | 4.27 |
| 06 | 0.15 | 1.64 | 10.93 |
| 07 | 1.15 | 2.25 | 1.96 |
| 08 | 0.21 | 0.43 | 2.05 |

Example 2

Example 2-1

Characterization of Immunocytes Induced by Co-Culturing Dendritic Cells Co-Pulsed in the Presence of ZOMETA™ and A27L and Responding Cells $1 \times 10^5$ each of the immature dendritic cells or the mature dendritic cells derived from peripheral blood prepared in Example 1 were added in a 24-well plate (SUMILON) such that the total amount was 1 ml. Further, ZOMETA™, which was an aminobisphosphonate agent, was added so as to achieve 0.01 μM, and/or A27L was added so as to achieve a final concentration of 2 μg/ml, followed by culturing at 37° C. under a condition of 5% $CO_2$ for about 24 hours. As a negative control, dendritic cells that were cultured without adding ZOMETA™ or the antigenic peptides were used. Then, after the culture for 12 hours using these pulsed dendritic cells as they were as the stimulating cells, further $2 \times 10^6$ responding cells were added, followed by co-culturing (responding cells: stimulating cells=20:1). The culture was conducted at about 37° C. under a condition of 5% $CO_2$ for 7 days or 14 days. Depending on cell proliferation, 1 to 100 U/ml of IL-2 was added to the co-cultured solution.

Using the total number of the cells that were proliferated respectively 7 days and 14 days after the start of co-culture, a labeled antibody and an antigen-specific tetramer, the ratio of antigen-specific CD8+ T cells and γδ T cells in all of the cells mentioned above was measured with a flow cytometer. The PE-labeled A27L tetramer (MBL) was added to the cells that had been washed in PBS after the completion of co-culture, and dyed in a shielded state at room temperature for 15 minutes. Thereafter, an FITC-labeled anti-CD8 antibody (BD Pharmingen) was added, followed by dyeing in a shielded state at 4° C. for 15 minutes. The ratio of the γδ T cells was determined using an FITC-labeled anti-TCR Vγ9 antibody, a PE-labeled anti-TCR pan α/β antibody and a PC5-labeled anti-CD3 antibody (all from Beckman Coulter). These antibodies were added to the cells that had been cultured and then washed in PBS, followed by dyeing in a shielded state at 4° C. for 15 minutes. As a negative control, an isotype of each of the antibodies was used. The cells were measured using EPICS XL.MCL, and the results of measurement were analyzed using EPICS 32.

The results are shown in Tables 5 and 6 below. As shown in Table 5, it was observed that the induction of the disease antigen-specific CD8+ CTLs when co-culturing the dendritic cells and the lymphocytes in the presence of 0.01 μM of ZOMETA™ and 2 μg/ml of A27L increased compared with that in the case of co-culturing the dendritic cells and the lymphocytes in the presence of A27L alone. These results suggest an adjuvant effect of ZOMETA™ for the induction of the disease antigen-specific CD8+ CTLs. Also, this adjuvant effect was confirmed to be greater in the immature dendritic cells.

Further, as shown in Table 6 below, it was confirmed that the induction of the γδ T cells by co-culturing the dendritic cells co-pulsed in the presence of 0.01 μM of ZOMETA™ and A27L and the lymphocytes increased as well.

[Table 5]

TABLE 5 a) Ratio (%) of disease antigen-specific CTLs induced by co-culturing dendritic cells pulsed using ZOMETA ™ and/or A27L and lymphocytes in all lymphocytes and b) the number of these cells

| State of dendritic cells | Culturing period | Sample used for pulsing dendritic cells | | |
|---|---|---|---|---|
| | | Antigenic peptide | ZOMETA ™ | Antigenic peptide + ZOMETA ™ |
| a) | | | | |
| Control | 0 day | | 0.03 | |
| Immature dendritic cells | 7 days | 0.15 | 0.08 | 1.64 |
| | 14 days | 0.05 | 0.26 | 5.08 |
| Mature dendritic cells | 7 days | 0.97 | 0.32 | 2.03 |
| | 14 days | 2.48 | 0.39 | 1.69 |
| b) | | | | |
| Control | 0 day | | $6.0 \times 10^2$ | |
| Immature dendritic cells | 7 days | $4.1 \times 10^3$ | $4.6 \times 10^3$ | $3.9 \times 10^3$ |
| | 14 days | $2.0 \times 10^3$ | $2.6 \times 10^3$ | $1.8 \times 10^5$ |
| Mature dendritic cells | 7 days | $3.0 \times 10^4$ | $1.4 \times 10^4$ | $5.2 \times 10^4$ |
| | 14 days | $1.1 \times 10^5$ | $3.5 \times 10^4$ | $7.4 \times 10^4$ |

The number of the cells was calculated by multiplying the total number of cells by the ratio.

[Table 6]

TABLE 6

Ratio (%) of γδ T cells induced by co-culturing dendritic cells co-pulsed using ZOMETA ™ and antigenic peptide and lymphocytes and the number of these cells

| State of dendritic cells | Culturing period | Sample used for co-pulsing dendritic cells A27L + ZOMETA ™ | |
|---|---|---|---|
| | | Ratio of γδ T cells | The number of γδ T cells |
| Before starting co-culturing | 0 day | 13.0 | $2.6 \times 10^5$ |
| Immature dendritic cells | 7 days | 25.7 | $6.1 \times 10^5$ |
| | 14 days | 26.9 | $9.7 \times 10^5$ |
| Mature dendritic cells | 7 days | 27.0 | $7.0 \times 10^5$ |
| | 14 days | 35.3 | $15.0 \times 10^5$ |

The number of the cells was calculated by multiplying the total number of cells by the ratio.

Example 2-2

Analysis of IFN-γ Production Ability of Immunocytes Induced by Co-Culturing Dendritic Cells Co-Pulsed in the Presence of ZOMETA™ and A27L and Responding Cells Subsequently, the IFN-γ production ability of immunocytes that were induced by the above-described co-culture was analyzed as follows.

70% ethanol was added to each well of MultiScreen plate (MILLIPORE) and removed within 2 minutes. Each well of the above-noted plate was washed five times in 200 μl of PBS. An anti-IFN-γ antibody for coating (clone: 1-D1K, MABTECH ELISpot for Human Interferon-γ kit) was diluted with PBS so as to achieve 15 μl/ml, and 100 μl thereof per well was added to the above-noted plate. This plate was left overnight at 4° C. This plate was washed four times in 200 μl/well of PBS. Then, 200 μl of an AIM-V medium supplemented with 10% FBS was added in each well, followed by blocking at room temperature for at least 30 minutes. The blocking medium was removed, and the plate was washed four times in 200 μl/well of PBS. A co-cultured cell population in each condition obtained by a method similar to the above-described co-culture was collected by centrifugation and washed twice in AIM-V.

For re-stimulation, 500 immature dendritic cells and A27L obtained in Example 1 were added to 2500 co-cultured cells that were collected, followed by pre-culturing at 37° C. under a condition of 5% $CO_2$ for 2 hours. The number of cells indicates the number per well of an assay plate. At the same time, pre-culture using the co-cultured cells alone and pre-culture using the dendritic cells and A27L alone were carried out as well. The culture volume was adjusted to be 100 μl per well. For each culture condition, 300 μl of culture, which corresponds to 3 wells, was performed. 100 μl per well of the cells pre-cultured under each condition was added into 3 wells in the plate that had been washed in PBS after blocking, and cultured overnight at 37° C. under a condition of 5% $CO_2$. The cultured cells were removed from the wells and washed five times in 200 μl/well of PBS. A biotin-labeled anti-IFN-γ antibody for detection (clone: 7-B61-1, MABTECH ELISPot™ for Human Interferon-γ kit) was diluted with PBS supplemented with 0.5% FBS so as to achieve 1 μg/ml, and 100 μl thereof per well was added. The plate was allowed to stand still at room temperature for 2 hours. This plate was washed five times in 200 μl/well of PBS. Streptavidin to which alkaline phosphatase was bound (MABTECH ELISPot™ for Human Interferon-γ kit) was diluted with PBS supplemented with 0.5% FBS so that 1:1000, and 100 μl thereof per well was added. The plate was left at room temperature for 1 hour. This plate was washed five times in 200 μl/well of PBS. Then, 100 μl of BCIP/NBTplus substrate solution (Wako) was added per well, which was left in a dark place until spots became visible. When the spots became visible to the naked eye, the plate was washed sufficiently in distilled water. After checking that a membrane in the plate is dry, the number of spots were measured using ELISPot™ reader (AID Autoimmun Diagnostika GmbH), and the data were analyzed with AID software version 3.1 (AID).

The results are shown in Table 7 below. As shown in this table, the number of spots, which indicated IFN-γ producing cells, increased most in the case where the co-cultured cell population of the dendritic cells co-pulsed with 0.01 μM of ZOMETA™ and 2 μg/ml of A27L and lymphocytes was re-stimulated using the dendritic cells pulsed with A27L. This result showed a correlation with the ratio (%) of the A27L tetramer-positive cells shown in Example 1 (see Table 4).

[Table 7]

TABLE 7

The number of IFN-γ producing cells obtained by co-culturing dendritic cells co-pulsed with ZOMETA ™ and antigenic peptide and lymphocytes in all of 2500 lymphocytes

| | Lymphocytes alone | | Lymphocytes + dendritic cells co-pulsed with peptides | |
|---|---|---|---|---|
| | Without ZOMETA ™ | With ZOMETA ™ | Without ZOMETA ™ | With ZOMETA ™ |
| Donor A | 1 | 4 | 55 | 100 |
| Donor B | 2 | 0 | 3 | 50 |

Example 3

Characterization of Immunocytes Induced by Co-Culturing Dendritic Cells in the Presence of ZOMETA™ and Apoptotic Cells Derived from Cancer Cell Line and Responding Cells From a healthy donor, 200 ml of peripheral blood was collected. Mononuclear cells were obtained from this peripheral blood of the healthy donor. At this time, a mononuclear cell layer was collected using a density gradient solution for blood cell separation. After several times of washing in order to remove platelets, etc. from the collected cells, CD14-positive cells were isolated as monocytes with MACS. From the obtained dendritic cell precursors, differentiation induction of dendritic cells was carried out. The medium was prepared by adding 500 U/ml of GM-CSF (IMMUNEX) and 500 U/ml of IL-4 (Osteogenetics GmbH) to AIM-V supplemented with 10% FBS. On day 5 to day 7 after starting culture, immature dendritic cells were obtained.

A cancer cell line derived from MART-1-positive melanoma was collected, placed in a 15 ml tube (BD Falcon) and centrifuged at 1500 rpm for 5 minutes. The resultant cell line in the form of pellets was suspended in 10 ml of an AIM-V medium and centrifuged at 1500 rpm for 5 minutes, followed by washing. The washing operation was repeated twice. The cell line collected in this manner was suspended again in AIM-V so as to achieve $1 \times 10^6$ cells/ml. Then, 10 μM of camptothecin (sigma) was added to the cell suspension and cultured at 37° C. under a condition of 5% $CO_2$ for 24 hours. The cultured cells were collected, placed in a 15 ml tube and centrifuged at 1500 rpm for 5 minutes. The resultant cell line in the form of pellets was suspended in 10 ml of an AIM-V medium and centrifuged at 1500 rpm for 5 minutes, followed by washing. The washing operation was repeated twice. The cells obtained by centrifugation and washing were used as apoptotic cells.

ZOMETA™, which was an aminobisphosphonate agent, was added to the suspension of the immature dendritic cells so as to achieve 0.01 μM, and/or a cancer cell line containing as many apoptotic cells as the dendritic cells was added thereto, followed by co-culturing for about 24 hours. As a control, dendritic cells that were cultured with the apoptotic cells alone for about 24 hours and dendritic cells that were cultured without adding ZOMETA™ or the apoptotic cells were used. Further, 100 U/ml of IL-6, 10 ng/ml of IL-1β, 10 ng/ml of TNFα and 1 μg/ml of $PGE_2$ were added to the immature dendritic cells that had been cultured for about 24 hours, and cultured further so as to obtain mature dendritic cells 48 hours later.

The mature dendritic cells obtained here were used as stimulating cells. $1 \times 10^5$ each of these stimulating cells were cultured with $2 \times 10^6$ responding cells such that the total amount was 1 ml in a 24-well plate (SUMILON) (responding cells:stimulating cells=20:1). Cells prepared by suspending those (a CD14-negative cell population, which was mainly a T cell population) remaining after isolation of the CD14-positive cells for preparing the dendritic cells in an AIM-V medium supplemented with 10% FBS and 10% dimethyl sulfoxide (DMSO), and freeze-preserving them were thawed, washed and used as responding cells. The culture was carried out at about 37° C. under a condition of 5% $CO_2$. 20 U/ml of IL-2 was added to this co-cultured solution. In the case where the cells were proliferated rapidly, 1 ml of an AIM-V medium supplemented with 40 U/ml of IL-2 and 10% FBS was added on day 4 to day 6.

Using the number of all lymphocytes that were proliferated 7, 11 and 14 days after the start of co-culture, a labeled antibody and an antigen-specific tetramer, the ratio of the antigen-specific CD8+ CTLs in all of the lymphocytes was measured with a flow cytometer. More specifically, A27L tetramer (MBL) that was labeled with PE was added to the cells that had been washed in PBS after cultured, followed by dyeing in a shielded state at room temperature for 15 minutes. Thereafter, an anti-CD8 antibody that was labeled with FITC (BD Pharmingen) was added, followed by dyeing in a shielded state at 4° C. for 15 minutes. As a negative control, an isotype of each of the antibodies was used. The cells were measured using EPICS XL.MCL, and the results of measurement were analyzed using EPICS 32.

The results are shown in Table 8 below. As shown in this table, in the case of pulse with the cell line containing the apoptotic cells, 0.01% of tetramer-positive cells were determined on day 11 of culture. Additionally, they were confirmed to be 0.14%, namely, increase by about 15 times by the addition of ZOMETA™.

[Table 8]

TABLE 8

Ratio of A27L antigen-specific CD8+ CTLs induced from activated dendritic cells co-pulsed with ZOMETA ™ and apoptotic cells

| | A27L-specific CD8+ CTLs | |
| --- | --- | --- |
| Dendritic cells | Ratio of CD8+ CTLs (%) | The number of CD8+ CTLs |
| Dendritic cells alone | 0.00 | 0 |
| Apoptotic cells + dendritic cells | 0.01 | $0.6 \times 10^3$ |
| Apoptotic cells + Zemeta + dendritic cells | 0.14 | $2.7 \times 10^3$ |

The number of the cells was calculated by multiplying the total number of cells by the ratio.

Example 4

Analysis of Cytotoxicity of Lymphocytes Cultured with Dendritic Cells Co-Pulsed with ZOMETA™ and Disease Antigenic Peptides Against Melanoma Cell Line $1 \times 10^5$ immature dendritic cells derived from peripheral blood prepared in Example 1 were added in each well of a 48-well plate. As a disease antigenic peptide, MART1 antigenic peptides A27L (ELAGIGILTV) were added in each well so as to achieve a final concentration of 2 Hg/ml. At the same time, the cells to which ZOMETA™ (Novartis), which was an aminobisphosphonate agent, was added as a zoledronic acid so as to achieve 0.01 μM and the cells to which no ZOMETA™ was added were prepared. In each well, $1 \times 10^6$ lymphocytes derived from the same donor were added, and cultured with the dendritic cells at 37° C. under a condition of 5% $CO_2$.

The lymphocytes were collected on day 13 to day 17 after the start of co-culture. A HLA-A*0201-positive and MART1-positive human melanoma cell line JCOCB was labeled with PKH-26 (Sigma) and used as target cells. The collected lymphocytes were used as effector cells. They were mixed with the target cells such that the effector cells:the target cells=5:1 or 20:1, and added in a 24-well plate. The culture was conducted for 4 hours at 37° C. under a condition of 5% $CO_2$.

The cells after co-culture were collected and washed in PBS that had been cooled with ice. After centrifugation, the cells were suspended in Annexin V Binding Buffer (BD Per-Mingen), and Annexin V and 7AAD (both from Beckman Coulter) were added thereto. After the reaction on the ice for 15 minutes, Annexin V Binding Buffer was added in an amount of 400 to 500 µl at each time, and the ratio (% of cytotoxicity) of apoptotic cells (Annexin V-positive cells) was measured by Flow Cytometry (Beckman Coulter).

Table 9 below shows the result of measuring the ratio (%) of A27L antigen-specific CD8+ CTLs induced from activated dendritic cells co-pulsed with A27L and ZOMETA™, the mean fluorescence intensity (MFI) at which the tetramer-positive cells are detected, and the ratio (%) of the apoptotic cells with reference to two donors. As shown in this table, in both of donor 1 and donor 2, lymphocytes stimulated using the activated dendritic cells co-pulsed with A27L and ZOMETA™ showed a higher ratio of the tetramer-positive cells than those stimulated with the dendritic cells pulsed with A27L alone. Also, the mean fluorescence intensity at which the tetramer-positive cells are detected was higher in the case of co-pulsing with A27L and ZOMETA™. Further, when the co-culture were carried out using the lymphocytes 13 to 17 days after the start of the culture as effector cells (E) and MART1-positive and HLA-A*0201-positive human melanoma cell line as target cells (T), the lymphocytes stimulated using the activated dendritic cells co-pulsed with A27L and ZOMETA™ showed a greater cytotoxicity to the target cells than those stimulated using the dendritic cells pulsed with A27L alone in both of the cases where the effector cells:the target cells=5:1 and 20:1.

[Table 9]

TABLE 9

Characteristics of A27L antigen-specific CD8+ CTLs induced from activated dendritic cells prepared by co-pulsing lymphocytes of two donors with A27L and ZOMETA ™

|  | Lymphocytes alone | Lymphocytes + dendritic cells pulsed with A27L | Lymphocytes + dendritic cells co-pulsed with A27L and ZOMETA ™ |
|---|---|---|---|
| Donor 1 | | | |
| Ratio (%) of A27L antigen-specific CD8+ CTLs | 0.00 | 0.27 | 0.27 |
| MFI | None | 21.2 | 36.9 |
| Ratio (%) of apoptotic cells  E/T = 5 | 5.9 | 9.3 | 10.2 |
| Ratio (%) of apoptotic cells  E/T = 20 | 7.4 | 13.7 | 19.9 |
| Donor 2 | | | |
| Ratio (%) of A27L antigen-specific CD8+ CTLs | 0.01 | 0.99 | 1.15 |
| MFI | None | 36.3 | 41.0 |
| Ratio (%) of apoptotic cells  E/T = 5 | 15.9 | 28.5 | 37.4 |
| Ratio (%) of apoptotic cells  E/T = 20 | 50.0 | 58.5 | 69.5 |

Example 5

Characterization of Immunocytes Induced from Dendritic Cells Co-Pulsed with ZOMETA™ and Disease Antigenic Peptides To a suspension of the immature dendritic cells or the mature dendritic cells derived from peripheral blood prepared in Example 1, ZOMETA™ (Novartis), which was an aminobisphosphonate agent, was added as a zoledronic acid so as to achieve 0 to 20 µM, and at the same time, EBV antigenic peptides BMLF1 (GLCTLVAML) (hereinafter, referred to as BMLF1) were added as disease antigenic peptides so as to achieve a final concentration of 2 µg/ml, followed by culturing at 37° C. under a condition of 5% $CO_2$ for about 12 hours, thus performing an activation treatment. As a negative control, dendritic cells that were cultured without adding ZOMETA™ or the antigenic peptides were used.

After about 12 hours of the culture, part of the activated dendritic cells that were co-pulsed with ZOMETA™ and the antigenic peptides were collected, placed in a 15 ml tube (BD Falcon) and centrifuged at 1500 rpm for 5 minutes. The resultant dendritic cells in the form of pellets were suspended in 10 ml of an AIM-V medium supplemented with 10% FBS and centrifuged at 1500 rpm for 5 minutes, followed by washing. The washing operation was repeated twice. The dendritic cells collected in this manner were used as stimulating cells. In other words, the activated dendritic cells that were co-pulsed with bisphosphonate and the disease antigenic peptides, the dendritic cells that were pulsed with either of them and the dendritic cells that were not pulsed with any of them were used as stimulating cells. Cells prepared by suspending those (a CD14-negative cell population, which was mainly a T cell population) remaining after isolation of the CD14-positive cells for preparing the dendritic cells in an AIM-V medium supplemented with 10% FBS and 10% dimethyl sulfoxide (DMSO), and freeze-preserving them were thawed, washed and used as responding cells. $1 \times 10^5$ each of the obtained stimulating cells (dendritic cells) were cultured with $1 \times 10^6$ responding cells such that the total amount was 1 ml in a 48-well plate (CORNING) (responding cells:dendritic cells=10:1). The co-culture was carried out at about 37° C. under a condition of 5% $CO_2$ for 7 days. When 20 U/ml of IL-2 was added to this co-cultured solution, the cells were proliferated more favorably. In the case where the cells were proliferated rapidly, 1 ml of an AIM-V medium supplemented with 40 U/ml of IL-2 and 10% FBS was added on day 4 to day 6. Then, 7 days after the start of the co-culture of the dendritic cells and the responding cells, the ratio of the BMLF1-specific CD8+ CTLs (the disease antigen-specific CD8+ CTLs) in all of the cells was measured with a flow cytometer using a labeled antibody and an antigen-specific tetramer.

The procedure of calculating the ratio of HLA-A*0201 BMLF1 tetramer-positive and CD8-positive cells is as follows: first, BMLF1 tetramer (MBL) that was labeled with PE was added to the cells that had been washed in PBS after cultured. After dyeing in a shielded state at room temperature for 15 minutes, an anti-CD8 antibody that was labeled with FITC (BD Pharmingen) was added, followed by dyeing in a shielded state at 4° C. for 15 minutes. As a control, an isotype of each of the antibodies was used. The cells were measured using EPICS XL.MCL, and the results of measurement were analyzed using EPICS 32.

The results are shown in Table 10 below. As shown in this table, it was confirmed that the activated dendritic cells that were co-pulsed with 0 to 20 μM of ZOMETA™ and BMLF1 induced the antigen-specific CD8+ CTLs. Further, the ratio of the antigen-specific CD8+ CTLs was confirmed to be about 3.2 times as high as that of CTLs induced from dendritic cells that were pulsed with peptides alone.

[Table 10]

TABLE 10

| Ratio (%) of disease antigen-specific CD8+ CTLs induced by culturing activated immature dendritic cells co-pulsed with BMLF1 and ZOMETA ™ and lymphocytes | | | | | | |
|---|---|---|---|---|---|---|
| ZOMETA ™ (μM) | 0 μM | 0.01 μM | 0.1 μM | 1 μM | 5 μM | 20 μM |
| Ratio of CTLs (%) | 0.33 | 0.54 | 0.56 | 0.58 | 0.75 | 0.72 |
| The total number of cells | $2.03 \times 10^6$ | $2.01 \times 10^6$ | $2.17 \times 10^6$ | $1.96 \times 10^6$ | $2.84 \times 10^6$ | $2.94 \times 10^6$ |
| The number of CTLs | 6715 | 10845 | 12130 | 11389 | 21266 | 21133 |

Example 6

Example 6-1

Production of Artificial Antigen-Presenting Cell Line

A human CD80 gene, which was a co-stimulatory molecule, was transfected by a lipofection method in a breast cancer-derived cell line: MDA-MB-231 (class I antigen HLA-A*0201) expressing MHC class I molecules, thus establishing a cell line MDA-MB/CD80 expressing human CD80 stably and constantly in MDA-MB-231 cells. As disclosed in US publication US-2005-0048646-A1, the cells in this MDA-MB/CD80 cell line function as antigen-presenting cells and are capable of inducing CTLs.

Example 6-2

Characterization of Immunocytes Induced from Artificial Antigen-Presenting Cells Co-Pulsed with ZOMETA™ and Disease Antigenic Peptides To a suspension of the artificial antigen-presenting cells MDA-MB/CD80 prepared as described above, ZOMETA™ (Novartis), which was an aminobisphosphonate agent, was added as a zoledronic acid so as to achieve 0.01 μM or 1 μM, and at the same time, MART-1 antigenic peptides A27L (ELAGIGILTV) were added as disease antigenic peptides so as to achieve a final concentration of 2 μg/ml, followed by culturing at 37° C. under a condition of 5% $CO_2$ for about 12 hours. As a negative control, MDA-MB/CD80 cells that were cultured without adding ZOMETA™ or the antigenic peptides were used.

After about 12 hours of culture, part of the activated MDA-MB/CD80 cells that were co-pulsed with ZOMETA™ and the antigenic peptides were collected, placed in a 15 ml tube (BD Falcon) and centrifuged at 1500 rpm for 5 minutes. The resultant MDA-MB/CD80 cells in the form of pellets were suspended in 10 ml of an AIM-V medium supplemented with 10% FBS and centrifuged at 1500 rpm for 5 minutes, followed by washing. The washing operation was repeated twice. The MDA-MB/CD80 cells collected in this manner were used as stimulating cells. In other words, the activated MDA-MB/CD80 cells that were co-pulsed with bisphosphonate and the disease antigenic peptides, the MDA-MB/CD80 cells that were pulsed with either of them and the MDA-MB/CD80 cells that were not pulsed with any of them were used as stimulating cells. As described above, cells prepared by suspending those (a CD14-negative cell population, which was mainly a T cell population, HLA-A*0201) remaining after isolation of the CD14-positive cells for preparing the dendritic cells in an AIM-V medium supplemented with 10% FBS and 10% dimethyl sulfoxide (DMSO), and freeze-preserving them were thawed, washed and used as responding cells.

$2 \times 10^5$ each of the stimulating cells (MDA-MB/CD80 cells) obtained as described above were cultured with $2 \times 10^6$ responding cells such that the total amount was 1 ml in a 24-well plate (SUMILON) (responding cells: stimulating cells=10:1). The co-culture was carried out at about 37° C. under a condition of 5% $CO_2$ for 7 days. When 20 U/ml of IL-2 was added to this co-cultured solution, the cells were proliferated more favorably. In the case where the cells were proliferated rapidly, 1 ml of an AIM-V medium supplemented with 40 U/ml of IL-2 and 10% FBS was added on day 4 to day 6. Then, 7 days after the start of the co-culture of the MDA-MB/CD80 cells and the responding cells, the ratio of the A27L-specific CD8+ CTLs (the disease antigen-specific CD8+ CTLs) in all of the cells was measured with a flow cytometer using a labeled antibody and an antigen-specific tetramer as described above.

The results are shown in Table 11 below. As shown in this table, it was confirmed that the activated MDA-MB/CD80 cells that were co-pulsed with 0.01 μM or 1 μM of ZOMETA™ and 2 μg/ml of A27L induced the antigen-specific CD8+ CTLs. Further, the ratio of the antigen-specific CD8+ CTLs in the case of using these activated MDA-MB/CD80 cells was confirmed to be about 6 times as high as that of CTLs induced from MDA-MB/CD80 cells that were pulsed with peptides alone.

[Table 11]

TABLE 11

| Ratio (%) of disease antigen-specific CD8+ CTLs induced by culturing activated MDA-MB/CD80 cells co-pulsed with ZOMETA ™ and A27L and lymphocytes Sample used for co-pulsed MDA-MB/CD80 cells | | |
|---|---|---|
| A27L | A27L + 0.01 μM of ZOMETA ™ | A27L + 1 μM of ZOMETA ™ |
| 0.12 | 0.75 | 0.98 |

INDUSTRIAL APPLICABILITY

As described above, the activated antigen-presenting cells of the present invention are capable of inducing the disease antigen-specific CD8+ CTLs very efficiently compared with the conventional dendritic cells that are pulsed with peptides alone, and of inducing the γδ T cells further. Accordingly, by administering the activated antigen-presenting cells of the present invention to a patient as a composition for administration, the disease antigen-specific CD8+ CTLs and/or the γδ T cells are induced in vivo, so that the effect of treating and preventing cancer and infectious disease can be expected. Furthermore, the activated antigen-presenting cells of the present invention can be utilized in vitro as a composition for inducing the disease antigen-specific CD8+ CTLs and/or the γδ T cells.

Japanese patent applications JP 2005-295598, filed Sep. 8, 2005, and JP 2006-112571, filed Apr. 14, 2006, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A method for activation treatment of an antigen-presenting cell, wherein the method comprises co-pulsing the antigen-presenting cell in vitro with a bisphosphonate and a disease antigen, wherein the antigen-presenting cell is a mature or immature dendritic cell.

2. The method for activation treatment of an antigen-presenting cell according to claim 1, wherein the bisphosphonate is a chemical compound of formula (I), a salt thereof or a hydrate thereof,

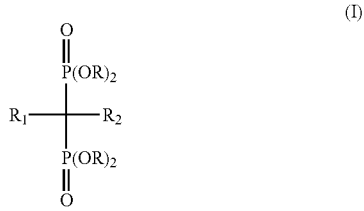

where R is selected from the group consisting of a hydrogen atom and a $C_1$-$C_{10}$ alkyl group, $R_1$ and $R_2$ are each, independently of one another, selected from the group consisting of a hydrogen atom, a halogen atom, a hydroxyl group, an amino group, a thiol group, an aryl group, a substituted aryl group, an alkyl group, a substituted alkyl group, a $C_1$-$C_{10}$ alkyl amino group, an aralkyl group, a cycloalkyl group and a heterocyclic group, or $R_1$ and $R_2$ form part of the same cyclic structure, and a substituent in $R_1$ and $R_2$ are selected from the group consisting of a halogen atom, a $C_1$-$C_{10}$ alkyl group, a hydroxyl group, a thiol group, an amino group, an alkoxy group, an aryl group, an arylthio group, an aryloxy group, an alkylthio group, a cycloalkyl group and a heterocyclic group.

3. The method for activation treatment of an antigen-presenting cell according to claim 1, wherein the bisphosphonate is at least one selected from the group consisting of a zoledronic acid, a pamidronic acid, an alendronic acid, a risedronic acid, an ibandronic acid, an incadronic acid, an etidronic acid, a salt thereof and a hydrate thereof.

4. The method for activation treatment of an antigen-presenting cell according to claim 1, wherein a concentration of the bisphosphonate in the co-pulse is 0.001 to 20 μM.

5. The method for activation treatment of an antigen presenting cell according to claim 4, wherein the concentration of the bisphosphonate in the co-pulse is 0.001 to 5 μM.

6. The method for activation treatment of an antigen-presenting cell according to claim 1, wherein the disease antigen is at least one selected from the group consisting of a cancer antigenic protein or peptide, an infectious disease antigenic protein or peptide, a lysed cancer cell, a lysed infectious disease cell, an apoptotic cell of a cancer cell, a necrotic cell of a cancer cell, an apoptotic cell of an infectious disease cell, and a necrotic cell of an infectious disease cell, or a heat-treated product thereof.

7. The method for activation treatment of an antigen-presenting cell according to claim 1, wherein a concentration of the disease antigen in the co-pulse is 0.1 to 20 μg/ml.

8. The method for activation treatment of an antigen-presenting cell according to claim 7, wherein the concentration of the disease antigen in the co-pulse is 0.1 to 2 μg/ml.

* * * * *

UNITED STATES PATENT AND TRADEMARK OFFICE
CERTIFICATE OF CORRECTION

PATENT NO.         : 8,609,410 B2                                      Page 1 of 1
APPLICATION NO.    : 12/066313
DATED              : December 17, 2013
INVENTOR(S)        : Nieda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 757 days.

Signed and Sealed this
Twenty-second Day of September, 2015

Michelle K. Lee
*Director of the United States Patent and Trademark Office*